United States Patent [19]
Burkholder et al.

[11] Patent Number: 5,864,045
[45] Date of Patent: *Jan. 26, 1999

[54] HETEROCYCLIC SUBSTITUTED PIPERAZINONE DERIVATIVES

[75] Inventors: Timothy P. Burkholder, Fairfield; Elizabeth M. Kudlacz; Tieu-Binh Le, both of Cincinnati, all of Ohio

[73] Assignee: Hoechst Marion Roussel, Inc., Cincinnati, Ohio

[ * ] Notice: This patent issued on a continued prosecution application filed under 37 CFR 1.53(d), and is subject to the twenty year patent term provisions of 35 U.S.C. 154(a)(2).

[21] Appl. No.: 67,386

[22] Filed: Apr. 27, 1998

Related U.S. Application Data

[62] Division of Ser. No. 878,695, Jun. 19, 1997, which is a continuation of Ser. No. 404,788, Mar. 15, 1995, abandoned.

[51] Int. Cl.⁶ ............... C07D 209/04; C07D 209/08
[52] U.S. Cl. ......................................... 548/491; 548/490
[58] Field of Search .................................. 548/490, 491

[56] References Cited

FOREIGN PATENT DOCUMENTS

| | | |
|---|---|---|
| 2271774 | 4/1994 | United Kingdom . |
| 9426735 | 5/1993 | WIPO . |
| WO 94/03483 | 2/1994 | WIPO . |

OTHER PUBLICATIONS

Khandelwal et al., Chemical Abstracts, vol. 113, No. 78332, (1990).

Lewis et al., J. Med. Chem., 38, pp. 923–933 (Mar. 17, 1995).

Roussi et al., Biochemical and Biophysical Research Communications, 176, pp. 894–901 (1991).

Maggi et al., J. Auton. Pharmacol, 13, pp. 23–93 (1993).

Primary Examiner—Johann Richter
Assistant Examiner—Jane C. Osweckí
Attorney, Agent, or Firm—David M. Stemerick

[57] ABSTRACT

The present invention relates to substituted piperazinone derivatives of formula (1) or stereoisomers, or pharmaceutically acceptable salts thereof and their use as tachykinin receptor antagonists. Such antagonists are useful in the treatment of tachykinin-mediated diseases and conditions disclosed herein including: asthma, cough, and bronchitis. The present invention also relates to intermediates useful in the preparation of compounds of formula (1).

14 Claims, No Drawings

HETEROCYCLIC SUBSTITUTED PIPERAZINONE DERIVATIVES

This application is a divisional of application Ser. No. 08/878,695, filed Jun. 19, 1997, which is a continuation of Ser. No. 08/404,788, filed Mar. 15, 1995, now abandoned, which is herein incorporated by reference.

The present invention relates to substituted piperazinone derivatives (herein referred to as compounds or compounds of formula (1)) or stereoisomers, or pharmaceutically acceptable salts thereof and their use as tachykinin receptor antagonists. Such antagonists are useful in the treatment of tachykinin-mediated diseases and conditions disclosed herein including: asthma, cough, and bronchitis. The present invention also relates to compounds of formula (2) useful as intermediates in the preparation of compounds of formula (1).

SUMMARY OF THE INVENTION

The present invention relates to compounds of formula (1):

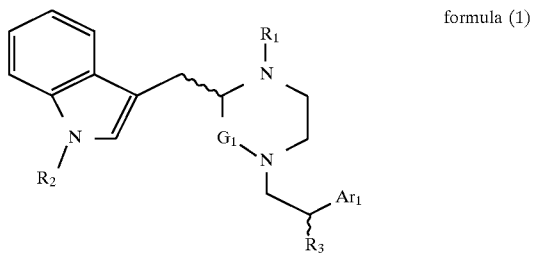

formula (1)

wherein $G_1$ is —CH$_2$— or —C(O)—;

Ar$_1$ is a radical chosen from the group:

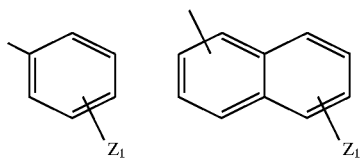

wherein $Z_1$ is from 1 to 3 substituents each independently chosen from the group consisting of hydrogen, halogen, benzyloxy, hydroxy, CF$_3$, C$_1$–C$_4$ alkyl, and C$_1$–C$_4$ alkoxy;

$R_1$ is hydrogen, a radical of the formula,

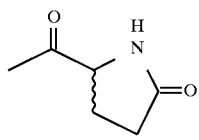

or —(CH$_2$)$_q$Ar$_2$, or —CH$_2$C(O)Ar$_2$
wherein
q is an integer from 1 to 4 and Ar$_2$ is a radical of the formula

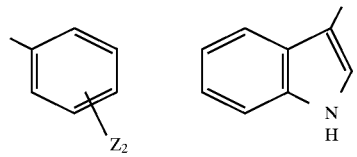

wherein $Z_2$ is from 1 to 3 substituents each independently chosen from the group consisting of hydrogen, halogen, benzyloxy, hydroxy, CF$_3$, C$_1$–C$_4$ alkyl, and C$_1$–C$_4$ alkoxy;

$R_2$ is hydrogen, C$_1$–C$_4$ alkyl, or —CHO;

$R_3$ is hydrogen or a radical chosen from the group

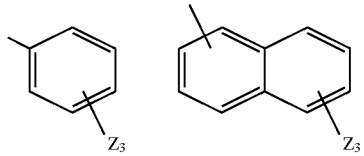

wherein $Z_3$ is from 1 to 3 substituents each independently chosen from the group consisting of hydrogen, halogen, benzyloxy, hydroxy, CF$_3$, C$_1$–C$_4$ alkyl, and C$_1$–C$_4$ alkoxy;

or stereoisomers, or pharmaceutically acceptable salt thereof.

In a further embodiment, the present invention relates to compounds, which are useful intermediates in the preparation of compounds of the formula (1), the compounds of formula (2):

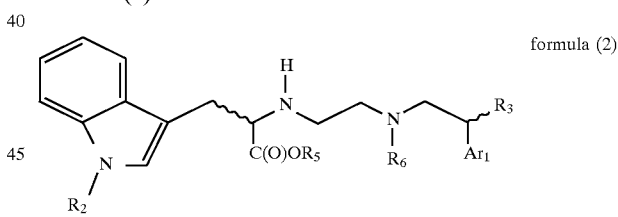

formula (2)

wherein

Ar$_1$ is a radical chosen from the group:

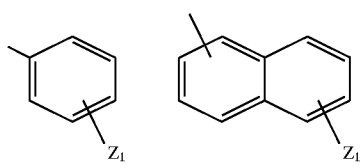

wherein $Z_1$ is from 1 to 3 substituents each independently chosen from the group consisting of hydrogen, halogen, benzyloxy, hydroxy, CF$_3$, C$_1$–C$_4$ alkyl, and C$_1$–C$_4$ alkoxy;

$R_2$ is hydrogen, C$_1$–C$_4$ alkyl, or —CHO;

$R_3$ is hydrogen or a radical chosen from the group

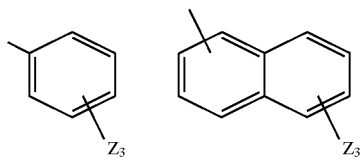

wherein
$Z_3$ is from 1 to 3 substituents each independently chosen from the group consisting of hydrogen, halogen, benzyloxy, hydroxy, $CF_3$, $C_1$–$C_4$ alkyl, and $C_1$–$C_4$ alkoxy;

$R_5$ is hydrogen, benzyl, or $C_1$–$C_4$ alkyl;

$R_6$ is hydrogen or —C(O)OR$_7$ wherein $R_7$ is benzyl or $C_1$–$C_4$ alkyl;

or stereoisomers, or pharmaceutically acceptable salt thereof.

As is appreciated by one of ordinary skill in the art the compounds of the formula (1) and formula (2) exist as stereoisomers. The Cahn-Ingold-Prelog designation of (R)- and (S)- for the stereochemistry of compounds represented by formula (1) and formula (2) depends on the nature of the substituents present. Any reference in this application to one of the compounds of the formula (1) and formula (2) is meant to encompass either specific stereoisomers or a mixture of stereoisomers. The specific stereoisomers can be prepared by stereospecific synthesis or can be separated and recovered by techniques known in the art, such as chromatography on chiral stationary phases, amide formation with a chiral acid followed by separation of the resultant diastereomeric amides and hydrolysis to the desired stereoisomer, or fractional recrystallization of addition salts formed by reagents used for that purpose, as described in "Enantiomers, Racemates, and Resolutions", J. Jacques, A. Collet, and S. H. Wilen, Wiley (1981).

As used in this application:
a) the term "halogen" refers to a fluorine atom, chlorine atom, bromine atom, or iodine atom;
b) the term "$C_1$–$C_4$ alkyl" refer to a branched or straight chained alkyl radical containing from 1 to 4 carbon atoms, such as methyl, ethyl, n-propyl, isopropyl, n-butyl, isobutyl, t-butyl, etc;
c) the term "$C_1$–$C_4$ alkoxy" refer to a straight or branched alkoxy group containing from 1 to 4 carbon atoms, such as methoxy, ethoxy, n-propoxy, isopropoxy, n-butoxy, isobutoxy, t-butoxy, etc;
d) the designation —C(O)— or C(O) refers to a carbonyl group of the formula:

e) the designation " ⁓ " refers to a bond for which the stereochemistry is not designated.
f) as used in the preparations and examples; the term "g" refers to grams; the term "mg" refers to milligrams; the term "kg" refers to kilograms; the term "mmol" refers to millimoles; the term "mL" refers to milliliters; the term "°C" refers to degrees Celsius the term "$R_f$" refers to retention factor; the term "mp" refers to melting point; the term "dec" refers to decomposition; the term "THF" refers to tetrahydrofuran; the term "DMF" refers to dimethylformamide; the term "$[\alpha]^{20}_D$" refer to specific rotation of the D line of sodium at 20° C. obtained in a 1 decimeter cell; the term "c" refers to concentration in g/mL; the term "DMSO" refers to dimethyl sulfoxide; the term "M" refers to molar; the term "HPLC" refers to high performance liquid chromatography; the term "HRMS" refers to high resolution mass spectrum;

g) by the designation

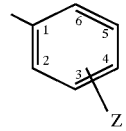

it is understood that the radical is attached at the 1-position and the substituent or substituents represented by Z can be attached in any of the 2, 3, 4, 5, or 6 positions;

h) by the designation

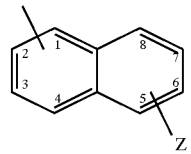

it is understood that the radical can be attached at the either the 1-position or the 2-position, it is further understood that when the radical is attached at the 1-position the substituent or substituents represented by Z can be attached in any of the 2, 3, 4, 5, 6, 7, or 8 positions and that when the radical is attached at the 2-position the substituent or substituents represented by Z can be attached in any of the 1, 3, 4, 5, 6, 7, or 8 positions;

i) the term "pharmaceutically acceptable salts thereof" refers to either an acid addition salt or a basic addition salt.

The expression "pharmaceutically acceptable acid addition salts" is intended to apply to any non-toxic organic or inorganic acid addition salt of the base compounds represented by formula (1) or formula (2). Illustrative inorganic acids which form suitable salts include hydrochloric, hydrobromic, sulphuric, and phosphoric acid and acid metal salts such as sodium monohydrogen orthophosphate, and potassium hydrogen sulfate. Illustrative organic acids which form suitable salts include the mono-, di-, and tricarboxylic acids. Illustrative of such acids are for example, acetic, glycolic, lactic, pyruvic, malonic, succinic, glutaric, fumaric, malic, tartaric, citric, ascorbic, maleic, hydroxymaleic, benzoic, hydroxy-benzoic, phenylacetic, cinnamic, salicyclic, 2-phenoxy-benzoic, p-toluenesulfonic acid, and sulfonic acids such as methane sulfonic acid and 2-hydroxyethane sulfonic acid. Such salts can exist in either a hydrated or substantially anhydrous form. In general, the acid addition salts of these compounds are soluble in water and various hydrophilic organic solvents, and which in comparison to their free base forms, generally demonstrate higher melting points.

The expression "pharmaceutically acceptable basic addition salts" is intended to apply to any non-toxic organic or inorganic basic addition salts of the compounds represented by formula (1) or formuala (2). Illustrative bases which form suitable salts include alkali metal or alkaline-earth metal hydroxides such as sodium, potassium, calcium, magnesium, or barium hydroxides; ammonia, and aliphatic, alicyclic, or aromatic organic amines such as methylamine, dimethylamine, trimethylamine, and picoline. Either the mono- or di-basic salts can be formed with those compounds.

As with any group of structurally related compounds which possesses a particular generic utility, certain groups and configurations are preferred for the compounds of formula (1) and formula (2) in their end-use application.

Preferred embodiments of formula (1) are given below:
1) Compounds in which $R_1$ is hydrogen or —$CH_2C(O)Ar_2$ are preferred;
2) Compounds in which $G_1$ —C(O)— are preferred;
3) Compounds in which $R_2$ is hydrogen are preferred;
4) Compounds in which $R_3$ is hydrogen are preferred;
5) Compounds in which $Ar_1$ is the radical

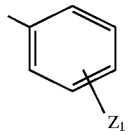

are preferred.

It is understood that further preferred embodiments of formula (1) can be selected by requiring one or more of the preferred embodiments 1 through 5 of formula (1) or by reference to examples given herein.

Preferred embodiments of formula (2) are given below:
1) Compounds in which $R_5$ is methyl are preferred;
2) Compounds in which $R_6$ is —C(O)O$R_7$ wherein $R_7$ is t-butyl are preferred;
3) Compounds in which $R_2$ is hydrogen are preferred;
4) Compounds in which $R_3$ is hydrogen are preferred;
5) Compounds in which $Ar_1$ is the radical

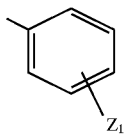

are preferred.

It is understood that further preferred embodiments of formula (2) can be selected by requiring one or more of the preferred embodiments 1 through 5 of formula (2) or by reference to examples given herein.

Illustrative of compounds encompassed by the present invention include the following. This list is meant to be representative only and is not intended to limit the scope of the invention in any way:

(R)-3-(1H-Indol-3-ylmethyl)-1-(2-phenyl-ethyl)-2-oxo-piperazine;
(S)-3-(1H-Indol-3-ylmethyl)-1-(2-phenyl-ethyl)-2-oxo-piperazine;
(R)-3-(1H-Indol-3-ylmethyl)-1-[2-[4-(benzyloxy)phenyl]ethyl]-2-oxo-piperazine;
(S)-3-(1H-Indol-3-ylmethyl)-1-[2-[4-(benzyloxy)phenyl]ethyl]-2-oxo-piperazine;
(R)-3-(1H-Indol-3-ylmethyl)-1-(2,2-bis-phenyl-ethyl)-2-oxo-piperazine;
(S)-3-(1H-Indol-3-ylmethyl)-1-(2,2-bis-phenyl-ethyl)-2-oxo-piperazine;
(R)-3-(1H-Indol-3-ylmethyl)-1-[2-[4-(hydroxy)phenyl]ethyl]]-2-oxo-piperazine;
(S)-3-(1H-Indol-3-ylmethyl)-1-[2-[4-(hydroxy)phenyl]ethyl]-2-oxo-piperazine;
(R)-3-(1H-Indol-3-ylmethyl)-4-[2-(1H-indol-3-yl)-2-oxo-ethyl]-1-(2-phenyl-ethyl)-2-oxo-piperazine;
(S)-3-(1H-Indol-3-ylmethyl)-4-[2-(1H-indol-3-yl)-2-oxo-ethyl]-1-(2-phenyl-ethyl)-2-oxo-piperazine;
(R)-3-(1H-Indol-3-ylmethyl)-4-[2-(1H-indol-3-yl)-2-oxo-ethyl]-1-(2,2-bis-phenyl-ethyl)-2-oxo-piperazine;
(S)-3-(1H-Indol-3-ylmethyl)-4-[2-(1H-indol-3-yl)-2-oxo-ethyl]-1-(2,2-bis-phenyl-ethyl)-2-oxo-piperazine;
(R)-3-(1H-Indol-3-ylmethyl)-4-[2-(1H-indol-3-yl)-2-oxo-ethyl]-1-[2-[4-(benzyloxy)phenyl]ethyl]-2-oxo-piperazine;
(S)-3-(1H-Indol-3-ylmethyl)-4-[2-(1H-indol-3-yl)-2-oxo-ethyl]-1-[2-[4-(benzyloxy)phenyl]ethyl]-2-oxo-piperazine;
(R)-3-(1H-Indol-3-ylmethyl)-4-[2-(1H-indol-3-yl)-2-oxo-ethyl]-1-[2-[4-(hydroxy)phenyl]ethyl]-2-oxo-piperazine;
(S)-3-(1H-Indol-3-ylmethyl)-4-[2-(1H-indol-3-yl)-2-oxo-ethyl]-1-[2-[4-(hydroxy)phenyl]ethyl]-2-oxo-piperazine;
(R)-3-(1H-Indol-3-ylmethyl)-4-[(S)-pyroglutamoyl]-1-(2-phenyl-ethyl)-2-oxo-piperazine;
(S)-3-(1H-Indol-3-ylmethyl)-4-[(S)-pyroglutamoyl]-1-(2-phenyl-ethyl)-2-oxo-piperazine;
(R)-3-(1H-Indol-3-ylmethyl)-4-[(R)-pyroglutamoyl]-1-(2-phenyl-ethyl)-2-oxo-piperazine;
(R)-3-(1H-Indol-3-ylmethyl)-4-[(R)-pyroglutamoyl]-1-(2-phenyl-ethyl)-2-oxo-piperazine;
(R)-3-(1H-Indol-3-ylmethyl)-4-[2-phenyl-2-oxo-ethyl]-1-(2-phenyl-ethyl)-2-oxo-piperazine;
(S)-3-(1H-Indol-3-ylmethyl)-4-[2-phenyl-2-oxo-ethyl]-1-(2-phenyl-ethyl)-2-oxo-piperazine;
(R)-3-(1H-Indol-3-ylmethyl)-4-[(phenyl)methyl]-1-(2-phenyl-ethyl)-2-oxo-piperazine;
(S)-3-(1H-Indol-3-ylmethyl)-4-[(phenyl)methyl]-1-(2-phenyl-ethyl)-2-oxo-piperazine;
(R)-3-(1H-Indol-3-ylmethyl)-1-(2-phenyl-ethyl)-piperazine;
(S)-3-(1H-Indol-3-ylmethyl)-1-(2-phenyl-ethyl)-piperazine;
(R)-3-(1H-Indol-3-ylmethyl)-1-(2-naphth-2-yl-ethyl)-2-oxo-piperazine;
(S)-3-(1H-Indol-3-ylmethyl)-1-(2-naphth-2-yl-ethyl)-2-oxo-piperazine;
(R)-3-(1H-Indol-3-ylmethyl)-1-(2-naphth-1-yl-ethyl)-2-oxo-piperazine;
(S)-3-(1H-Indol-3-ylmethyl)-1-(2-naphth-1-yl-ethyl)-2-oxo-piperazine;
(R)-3-(1H-Indol-3-ylmethyl)-1-[2-[4-(chloro)phenyl]ethyl]-2-oxo-piperazine;
(S)-3-(1H-Indol-3-ylmethyl)-1-[2-[4-(chloro)phenyl]ethyl]-2-oxo-piperazine;
(R)-3-(1H-Indol-3-ylmethyl)-1-[2-[4-(fluoro)phenyl]ethyl]-2-oxo-piperazine;
(S)-3-(1H-Indol-3-ylmethyl)-1-[2-[4-(fluoro)phenyl]ethyl]-2-oxo-piperazine;
(R)-3-(1H-Indol-3-ylmethyl)-1-[2-[4-(methyl)phenyl]ethyl]-2-oxo-piperazine;
(S)-3-(1H-Indol-3-ylmethyl)-1-[2-[4-(methyl)phenyl]ethyl]-2-oxo-piperazine;
(R)-3-(1H-Indol-3-ylmethyl)-1-[2-[4-(methoxy)phenyl]ethyl]-2-oxo-piperazine;
(S)-3-(1H-Indol-3-ylmethyl)-1-[2-[4-(methoxy)phenyl]ethyl]-2-oxo-piperazine;
(R)-3-(1H-Indol-3-ylmethyl)-1-[2-[4-(trifluoromethyl)phenyl]ethyl]-2-oxo-piperazine; (S)-3-(1H-Indol-3-ylmethyl)-1-[2-[4-(trifluoromethyl)phenyl]ethyl]-2-oxo-piperazine;
(R)-3(R)-3-(1H-Indol-3-ylmethyl)-1-[2-[2-(benzyloxy)phenyl]ethyl]-2-oxo-piperazine;
(S)-3-(1H-Indol-3-ylmethyl)-1-[2-[2-(benzyloxy)phenyl]ethyl]-2-oxo-piperazine;
(R)-3-(1H-Indol-3-ylmethyl)-1-[2-[2-(hydroxy)phenyl]ethyl]]-2-oxo-piperazine;

(S)-3-(1H-Indol-3-ylmethyl)-1-[2-[2-(hydroxy)phenyl]
ethyl]-2-oxo-piperazine;
(R)-3-(1H-Indol-3-ylmethyl)-1-[2-[3-(benzyloxy)phenyl]
ethyl]-2-oxo-piperazine;
(S)-3-(1H-Indol-3-ylmethyl)-1-[2-[3-(benzyloxy)phenyl]
ethyl]-2-oxo-piperazine;
(R)-3-(1H-Indol-3-ylmethyl)-1-[2-[3-(hydroxy)phenyl]
ethyl]]-2-oxo-piperazine;
(S)-3-(1H-Indol-3-ylmethyl)-1-[2-[3-(hydroxy)phenyl]
ethyl]-2-oxo-piperazine;
(R)-3-(1H-Indol-3-ylmethyl)-1-[2-[2-(chloro)phenyl]ethyl]-
2-oxo-piperazine;
(S)-3-(1H-Indol-3-ylmethyl)-1-[2-[2-(chloro)phenyl]ethyl]-
2-oxo-piperazine;
(R)-3-(1H-Indol-3-ylmethyl)-1-[2-[2-(fluoro)phenyl]ethyl]-
2-oxo-piperazine;
(S)-3-(1H-Indol-3-ylmethyl)-1-[2-[2-(fluoro)phenyl]ethyl]-
2-oxo-piperazine;
(R)-3-(1H-Indol-3-ylmethyl)-1-[2-[2-(methyl)phenyl]ethyl]
-2-oxo-piperazine;
(S)-3-(1H-Indol-3-ylmethyl)-1-[2-[2-(methyl)phenyl]ethyl]
-2-oxo-piperazine;
(R)-3-(1H-Indol-3-ylmethyl)-1-[2-[2-(methoxy)phenyl]
ethyl]-2-oxo-piperazine;
(S)-3-(1H-Indol-3-ylmethyl)-1-[2-[2-(methoxy)phenyl]
ethyl]-2-oxo-piperazine;
(R)-3-(1H-Indol-3-ylmethyl)-1-[2-[2-(trifluoromethyl)
phenyl]ethyl]-2-oxo-piperazine;
(S)-3-(1H-Indol-3-ylmethyl)-1-[2-[2-(trifluoromethyl)
phenyl]ethyl]-2-oxo-piperazine;
2-[(R)-2-(1H-Indol-3-yl)-1-carboxymethyl-ethylamino]-N-
(t-butoxycarbonyl)-N-(2-phenyl-ethyl)-ethylamine;
2-[(S)-2-(1H-Indol-3-yl)-1-carboxymethyl-ethylamino]-N-
(t-butoxycarbonyl)-N-(2-phenyl-ethyl)-ethylamine;
2-[(R)-2-(1H-Indol-3-yl)-1-carboxymethyl-ethylamino]-N-
(t-butoxycarbonyl)-N-[2-[(4-benzyloxy)phenyl-ethyl]]-
ethylamine;
2-[(S)-2-(1H-Indol-3-yl)-1-carboxymethyl-ethylamino]-N-
(t-butoxycarbonyl)-N-[2-[(4-benzyloxy)phenyl-ethyl]]-
ethylamine;
2-[(R)-2-(1H-Indol-3-yl)-1-carboxymethyl-ethylamino]-N-
(t-butoxycarbonyl)-N-(2,2-bis-phenyl-ethyl)]-
ethylamine;
2-[(S)-2-(1H-Indol-3-yl)-1-carboxymethyl-ethylamino]-N-
(t-butoxycarbonyl)-N-(2,2-bis-phenyl-ethyl)]-
ethylamine;
2-[(R)-2-(1H-Indol-3-yl)-1-carboxymethyl-ethylamino]-N-
(t-butoxycarbonyl)-N-(2-naphth-2-yl-ethyl)-ethylamine;
2-[(S)-2-(1H-Indol-3-yl)-1-carboxymethyl-ethylamino]-N-
(t-butoxycarbonyl)-N-(2-naphth-2-yl-ethyl)-ethylamine;
p0 2-[(R)-2-(1H-Indol-3-yl)-1-carboxymethyl-
ethylamino]-N-(t-butoxycarbonyl)-N-(2-naphth-1-yl-
ethyl)-ethylamine;
2-[(S)-2-(1H-Indol-3-yl)-1-carboxymethyl-ethylamino]-N-
(t-butoxycarbonyl)-N-(2-naphth-1-yl-ethyl)-ethylamine;
2-[(R)-2-(1H-Indol-3-yl)-1-carboxymethyl-ethylamino]-N-
(t-butoxycarbonyl)-N-[(2-[4-(chloro)phenyl-ethyl]]-
ethylamine;
2-[(S)-2-(1H-Indol-3-yl)-1-carboxymethyl-ethylamino]-N-
(t-butoxycarbonyl)-N-[(2-[4-(chloro)phenyl-ethyl]]-
ethylamine;
2-[(S)-2-(1H-Indol-3-yl)-1-carboxymethyl-ethylamino]-N-
(t-butoxycarbonyl)-N-[(2-[4-(fluoro)phenyl-ethyl]]-
ethylamine;
2-[(R)-2-(1H-Indol-3-yl)-1-carboxymethyl-ethylamino]-N-
(t-butoxycarbonyl)-N-[(2-[4-(fluoro)phenyl-ethyl]]-
ethylamine;
2-[(S)-2-(1H-Indol-3-yl)-1-carboxymethyl-ethylamino]-N-
(t-butoxycarbonyl)-N-[(2-[4-(methyl)phenyl-ethyl]]-
ethylamine;
2-[(R)-2-(1H-Indol-3-yl)-1-carboxymethyl-ethylamino]-N-
(t-butoxycarbonyl)-N-[(2-[4-(methyl)phenyl-ethyl]]-
ethylamine;
2-[(S)-2-(1H-Indol-3-yl)-1-carboxymethyl-ethylamino]-N-
(t-butoxycarbonyl)-N-[(2-[4-(methyloxy)phenyl-ethyl]]-
ethylamine;
2-[(R)-2-(1H-Indol-3-yl)-1-carboxymethyl-ethylamino]-N-
(t-butoxycarbonyl)-N-[(2-[4-(methyloxy)phenyl-ethyl]]-
ethylamine;
2-[(S)-2-(1H-Indol-3-yl)-1-carboxymethyl-ethylamino]-N-
(t-butoxycarbonyl)-N-[(2-[4-(triflurormethyl)phenyl-
ethyl]]-ethylamine;
2-[(R)-2-(1H-Indol-3-yl)-1-carboxymethyl-ethylamino]-N-
(t-butoxycarbonyl)-N-((2-[4-(triflurormethyl)phenyl-
ethyl]]-ethylamine;
2-[(S)-2-(1H-Indol-3-yl)-1-carboxymethyl-ethylamino]-N-
(t-butoxycarbonyl)-N-[(2-[2-(benzyloxy)phenyl-ethyl]]-
ethylamine;
2-[(R)-2-(1H-Indol-3-yl)-1-carboxymethyl-ethylamino]-N-
(t-butoxycarbonyl)-N-[(2-[2-(benzyloxy)phenyl-ethyl]]-
ethylamine;
2-[(S)-2-(1H-Indol-3-yl)-1-carboxymethyl-ethylamino]-N-
(t-butoxycarbonyl)-N-[(2-[3-(benzyloxy)phenyl-ethyl]]-
ethylamine;
2-[(R)-2-(1H-Indol-3-yl)-1-carboxymethyl-ethylamino]-N-
(t-butoxycarbonyl)-N-[(2-[3-(benzyloxy)phenyl-ethyl]]-
ethylamine;
2-[(R)-2-(1H-Indol-3-yl)-1-carboxymethyl-ethylamino]-N-
(t-butoxycarbonyl)-N-[(2-[2-(chloro)phenyl-ethyl]]-
ethylamine;
2-[(S)-2-(1H-Indol-3-yl)-1-carboxymethyl-ethylamino]-N-
(t-butoxycarbonyl)-N-[(2-[2-(chloro)phenyl-ethyl]]-
ethylamine;
2-[(R)-2-(1H-Indol-3-yl)-1-carboxymethyl-ethylamino]-N-
(t-butoxycarbonyl)-N-[(2-[2-(fluoro)phenyl-ethyl]]-
ethylamine;
2-[(S)-2-(1H-Indol-3-yl)-1-carboxymethyl-ethylamino]-N-
(t-butoxycarbonyl)-N-[(2-[2-(fluoro)phenyl-ethyl]]-
ethylamine;
2-[(S)-2-(1H-Indol-3-yl)-1-carboxymethyl-ethylamino]-N-
(t-butoxycarbonyl)-N-[(2-[2-(methyl)phenyl-ethyl]]-
ethylamine;
2-[(R)-2-(1H-Indol-3-yl)-1-carboxymethyl-ethylamino]-N-
(t-butoxycarbonyl)-N-[(2-[2-(methyl)phenyl-ethyl]]-
ethylamine;
2-[(S)-2-(1H-Indol-3-yl)-1-carboxymethyl-ethylamino]-N-
(t-butoxycarbonyl)-N-[(2-[2-(methyloxy)phenyl-ethyl]]-
ethylamine;
2-[(R)-2-(1H-Indol-3-yl)-1-carboxymethyl-ethylamino]-N-
(t-butoxycarbonyl)-N-[(2-[2-(methyloxy)phenyl-ethyl]]-
ethylamine;
2-[(S)-2-(1H-Indol-3-yl)-1-carboxymethyl-ethylamino]-N-
(t-butoxycarbonyl)-N-[(2-[2-(triflurormethyl)phenyl-
ethyl]]-ethylamine;
2-[(R)-2-(1H-Indol-3-yl)-1-carboxymethyl-ethylamino]-N-
(t-butoxycarbonyl)-N-[(2-[2-(triflurormethyl)phenyl-
ethyl]]-ethylamine;
2-[(R)-2-(1H-Indol-3-yl)-1-carboxymethyl-ethylamino]-N-
(2-phenyl-ethyl)-ethylamine;
2-[(S)-2-(1H-Indol-3-yl)-1-carboxymethyl-ethylamino]-N-
(2-phenyl-ethyl)-ethylamine;
2-[(R)-2-(1H-Indol-3-yl)-1-carboxymethyl-ethylamino]-N-
2-[(4-benzyloxy)phenyl-ethyl]]-ethylamine;
2-[(S)-2-(1H-Indol-3-yl)-1-carboxymethyl-ethylamino]-N-
2-[(4-benzyloxy)phenyl-ethyl]]-ethylamine;

2-[(R)-2-(1H-Indol-3-yl)-1-carboxymethyl-ethylamino]-N-(2,2-bis-phenyl-ethyl)]-ethylamine;
2-[(S)-2-(1H-Indol-3-yl)-1-carboxymethyl-ethylamino]-N-(2,2-bis-phenyl-ethyl)]-ethylamine;
2-[(R)-2-(1H-Indol-3-yl)-1-carboxymethyl-ethylamino]-N-(2-naphth-2-yl-ethyl)-ethylamine;
2-[(S)-2-(1H-Indol-3-yl)-1-carboxymethyl-ethylamino]-N-(2-naphth-2-yl-ethyl)-ethylamine;
2-[(R)-2-(1H-Indol-3-yl)-1-carboxymethyl-ethylamino]-N-(2-naphth-1-yl-ethyl)-ethylamine; 2-[(S)-2-(1H-Indol-3-yl)-1-carboxymethyl-ethylamino]-N-(2-naphth-1-yl-ethyl)-ethylamine;
2-[(R)-2-(1H-Indol-3-yl)-1-carboxymethyl-ethylamino]-N-[(2-[4-(chloro)phenyl-ethyl]]-ethylamine;
2-[(S)-2-(1H-Indol-3-yl)-1-carboxymethyl-ethylamino]-N-[(2-[4-(chloro)phenyl-ethyl]]-ethylamine;
2-[(S)-2-(1H-Indol-3-yl)-1-carboxymethyl-ethylamino]-N-[(2-[4-(fluoro)phenyl-ethyl]]-ethylamine;
2-[(R)-2-(1H-Indol-3-yl)-1-carboxymethyl-ethylamino]-N-[(2-[4-(fluoro)phenyl-ethyl]]-ethylamine;
2-[(S)-2-(1H-Indol-3-yl)-1-carboxymethyl-ethylamino]-N-[(2-[4-(methyl)phenyl-ethyl]]-ethylamine;
2-[(R)-2-(1H-Indol-3-yl)-1-carboxymethyl-ethylamino]-N-[(2-[4-(methyl)phenyl-ethyl]]-ethylamine;
2-[(S)-2-(1H-Indol-3-yl)-1-carboxymethyl-ethylamino]-N-[(2-[4-(methyloxy)phenyl-ethyl]]-ethylamine;
2-[(R)-2-(1H-Indol-3-yl)-1-carboxymethyl-ethylamino]-N-[(2-[4-(methyloxy)phenyl-ethyl]]-ethylamine;
2-[(S)-2-(1H-Indol-3-yl)-1-carboxymethyl-ethylamino]-N-[(2-[4-(triflurormethyl)phenyl-ethyl]]-ethylamine;
2-[(R)-2-(1H-Indol-3-yl)-1-carboxymethyl-ethylamino]-N-[(2-[4-(triflurormethyl)phenyl-ethyl]]-ethylamine;
2-[(S)-2-(1H-Indol-3-yl)-1-carboxymethyl-ethylamino]-N-[(2-[2-(benzyloxy)phenyl-ethyl]]-ethylamine;
2-[(R)-2-(1H-Indol-3-yl)-1-carboxymethyl-ethylamino]-N-[(2-[2-(benzyloxy)phenyl-ethyl]]-ethylamine;
2-[(S)-2-(1H-Indol-3-yl)-1-carboxymethyl-ethylamino]-N-[(2-[3-(benzyloxy)phenyl-ethyl]]-ethylamine;
2-[(R)-2-(1H-Indol-3-yl)-1-carboxymethyl-ethylamino]-N-[(2-[3-(benzyloxy)phenyl-ethyl]]-ethylamine;
2-[(R)-2-(1H-Indol-3-yl)-1-carboxymethyl-ethylamino]-N-[(2-[2-(chloro)phenyl-ethyl]]-ethylamine;
2-[(S)-2-(1H-Indol-3-yl)-1-carboxymethyl-ethylamino]-N-[(2-[2-(chloro)phenyl-ethyl]]-ethylamine;
2-[(S)-2-(1H-Indol-3-yl)-1-carboxymethyl-ethylamino]-N-[(2-[2-(fluoro)phenyl-ethyl]]-ethylamine;
2-[(R)-2-(1H-Indol-3-yl)-1-carboxymethyl-ethylamino]-N-[(2-[2-(fluoro)phenyl-ethyl]]-ethylamine;
2-[(S)-2-(1H-Indol-3-yl)-1-carboxymethyl-ethylamino]-N-[(2-[2-(methyl)phenyl-ethyl]]-ethylamine;
2-[(R)-2-(1H-Indol-3-yl)-1-carboxymethyl-ethylamino]-N-[(2-[2-(methyl)phenyl-ethyl]]-ethylamine;
2-[(S)-2-(1H-Indol-3-yl)-1-carboxymethyl-ethylamino]-N-[(2-[2-(methyloxy)phenyl-ethyl]]-ethylamine;
2-[(R)-2-(1H-Indol-3-yl)-1-carboxymethyl-ethylamino]-N-[(2-[2-(methyloxy)phenyl-ethyl]]-ethylamine;
2-[(S)-2-(1H-Indol-3-yl)-1-carboxymethyl-ethylamino]-N-[(2-[2-(triflurormethyl)phenyl-ethyl]]-ethylamine;
2-[(R)-2-(1H-Indol-3-yl)-1-carboxymethyl-ethylamino]-N-[(2-[2-(triflurormethyl)phenyl-ethyl]]-ethylamine.

A general synthetic procedure is set forth in Scheme A for preparing these compounds of formula (1). The reagents and starting materials are readily available to one of ordinary skill in the art. In Scheme A, all substituents, unless otherwise indicated, are as previously defined.

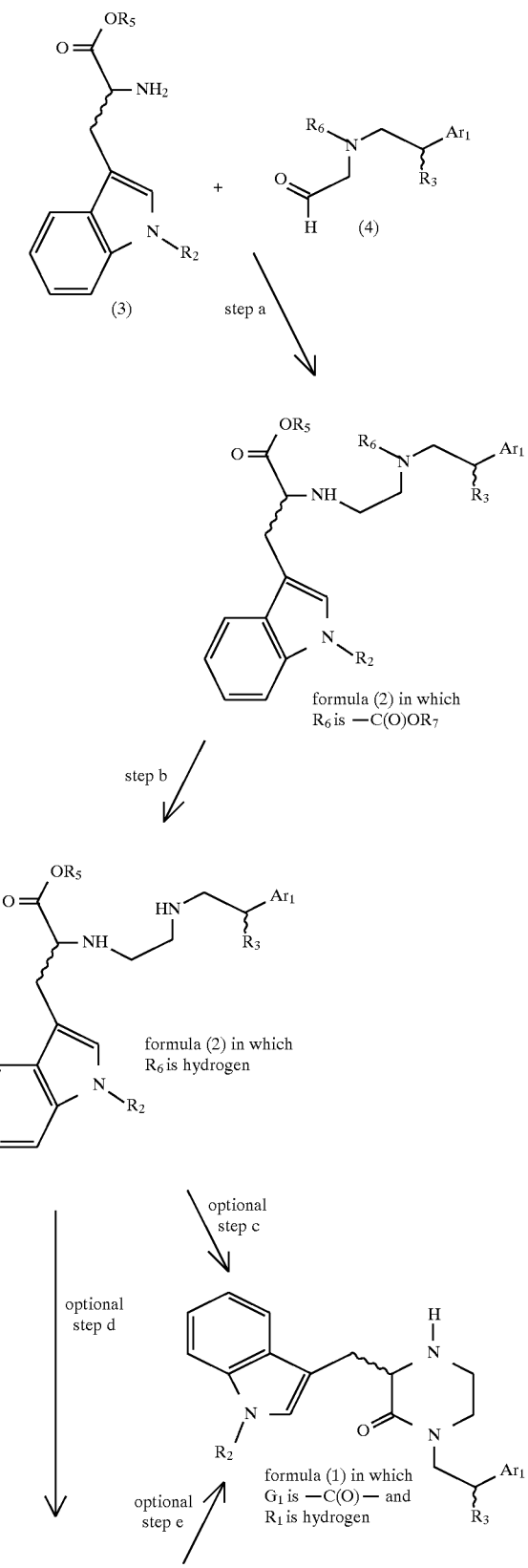

SCHEME A

-continued
SCHEME A

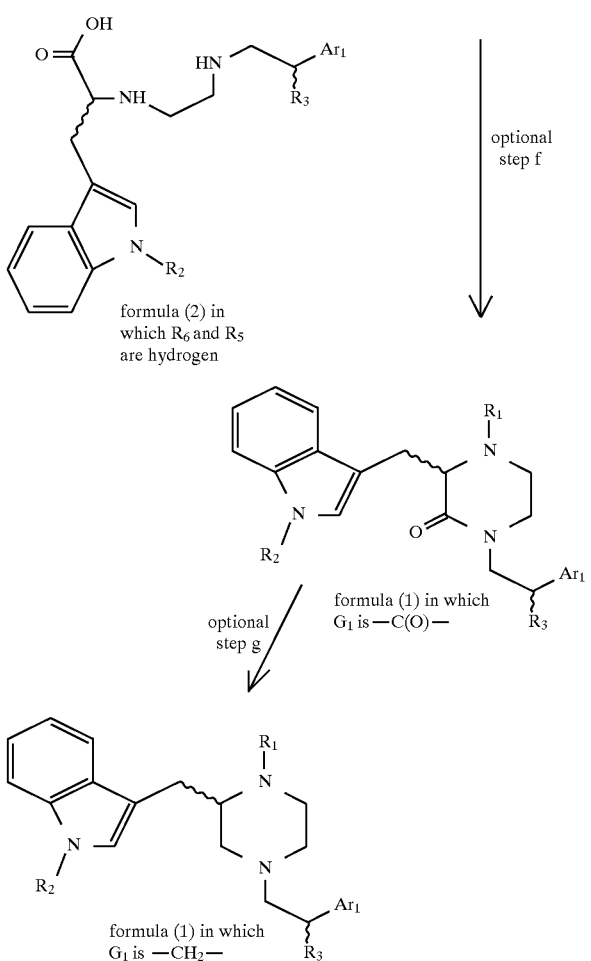

In Scheme A, step a, an appropriate amine of structure (3) or a salt thereof and an appropriate aldehyde of structure (4) are contacted with in a reductive amination to give a compound of formula (2) in which $R_6$ is —C(O)OR$_7$.

An appropriate amine of structure (3) is one in which $R_2$ and $R_5$ are as defined for formula (2) and the stereochemistry is as desired in the final product of formula (1). For the preparation of compounds of formula (1), an amine of structure (3) in which $R_5$ is methyl is preferred. An appropriate aldehyde of structure (4) is one in which the $Ar_1$ and $R_3$ are as desired in the product of formula (1) or give rise after deprotection to a group as desired in the final product of formula (1) and $R_6$ is —C(O)OR$_7$ as defined for formula (2). For the preparation of compounds of formula (1), an aldehyde of structure (4) in which $R_7$ is t-butyl is preferred.

For example, an appropriate aldehyde of structure (4) is contacted with an appropriate amine of structure (3) or a salt thereof in a reductive amination. The reaction is carried out using a molar excess of a suitable reducing agent such as sodium borohydride or sodium cyanoborohydride with sodium cyanoborohydride being preferred. The reaction is carried out in a suitable solvent, such as methanol, dimethylformamide, dichloromethane, methanol/ dimethylformamide mixtures, and methanol/ dichloromethane mixtures. The reaction is carried out at temperatures of from 0° C. to 50° C. The reaction generally requires 24 to 72 hours. The product can be isolated and purified by techniques well known in the art, such as extraction, evaporation, chromatography, and recrystallization.

In Scheme A, step b, a compound of formula (2) in which $R_6$ is —C(O)OR$_7$ is deprotected to give a compound of formula (2) or a salt thereof in which $R_6$ is hydrogen.

For example, a compound of formula (2) in which $R_6$ is —C(O)OR$_7$ in which $R_7$ is t-butyl is reacted with a protic acid, such as hydrochloric acid or trifluoroacetic acid. The reaction is carried out in a solvent, such as water, ethyl acetate, dioxane, methanol, or ethanol. The reaction generally requires from 1 to 48 hours and is carried out at temperatures of from −20° C. to 50° C. The product can be isolated and purified by techniques well known in the art, such as extraction, evaporation, chromatography, and recrystallization. The removal of protecting groups other that —C(O)OR$_7$ in which $R_7$ is t-butyl is well known and appreciated in the art.

In Scheme A, optional step c, a compound of formula (2) in which $R_6$ is hydrogen or a salt thereof undergoes a cyclization reaction to give a compound of the formula (1) in which $G_1$ is —C(O)— and $R_1$ is hydrogen.

For example, a compound of formula (2) in which $R_6$ is hydrogen or a salt thereof is cyclized. The reaction is carried out at the reflux temperature of a suitable solvent, such as toluene or xylene. When a salt of a compound of formula (2) in which $R_6$ is hydrogen is used the reaction is carried out in the presence of about an equimolar amount of a suitable base, such as triethylamine, diisopropylethylamine, or pyridine. The reaction generally requires from 12 to 72 hours. The product can be isolated and purified by techniques well known in the art, such as extraction, evaporation, chromatography, and recrystallization.

Alternately, the compounds of formula (1) can be prepared form compounds of formula (2) by Scheme A, optional steps d and e, as taught below.

In Scheme A, optional step d, a compound of formula (2) in which $R_5$ is $C_1$–$C_4$ alkyl is hydrolyzed to give a compound of formula (2) in which $R_5$ is hydrogen. The hydrolysis of esters, such as those described in *Protecting Groups in Organic Synthesis* by T. Greene is well known and appreciated in the art.

For example, a compound of formula (2) in which $R_5$ is $C_1$–$C_4$ alkyl is reacted with a suitable hydrolyzing agent, such as sodium hydroxide, potassium hydroxide, lithium hydroxide, or sodium carbonate. The reaction is carried out in a suitable solvent, such as water or water/methanol mixtures, water/ethanol mixtures, water/tetrahydrofuran mixtures. The reactions are carried out at temperatures of from 0° C. to the refluxing temperature of the solvent and generally require from 30 minutes to 48 hours. The product can be isolated and purified by techniques well known in the art, such as acidification, extraction, evaporation, chromatography, and recrystallization.

In Scheme A, optional step e, a compound of formula (2) in which $R_6$ and $R_5$ are hydrogen or a salt thereof undergoes a cyclization reaction to give a compound of the formula (1) in which G1 is —C(O)— and $R_1$ is hydrogen. This cyclization reaction may proceed through an activated intermediate, such as a mixed anhydride or a (O)—hydroxybenzotriazole, which may be prepared but is not necessarily isolated before the cyclization.

For example, a compound of formula (2) in which $R_6$ and $R_5$ are hydrogen or a salt thereof is contacted with about an equimolar amount of 1-hydroxybenzotriazole hydrate in the presence of a slight molar excess of a suitable coupling agent, such as dicyclohexylcarbodiimide or 1-(3-dimethyaminopropyl)-3-ethylcarbodiimide. The reaction is carried out in the presence of a suitable base, such as diisopropylethyl amine. The reaction is carried out in a suitable solvent, such as dichloromethane, chloroform, ethyl acetate, and dimethylformamide; and at temperatures of from −50° C. to the refluxing temperature of the solvent. The reaction generally requires from 1 hour to 48 hours. The product can be isolated and purified by techniques well known in the art, such as extraction, evaporation, chromatography, and recrystallization.

As is appreciated to one skilled in the art, in Scheme A the order in which optional step d and step b are carried out will depend on the compound of formula (2) which is used and the compound of formula (1) which is desired. For some of the compounds of formula (2), it may be advantageous to carry out an ester hydrolysis, optional step d, before the removal of the group $R_6$, which is —C(O)$OR_7$, in step b.

In Scheme A, optional step f, a compound of formula (1) may be deprotected or modified to give a compound of formula (1).

A deprotection reaction encompasses the hydrolysis of esters, the removal of a hydroxy protecting group, the removal of an indole protecting group, or the removal of an amino protecting group. The selection, use, and removal of protecting groups utilizing suitable protecting groups such as those described in *Protecting Groups in Organic Synthesis* by T. Greene is well known and appreciated in the art.

A modification reaction encompasses the formation of amides, the alkylation of an amine, an addition reaction to an indole nitrogen, and the formation of an amidate. A compound of formula (1) in which $R_1$ is hydrogen is alkylated with an appropriate alkylating agent to give a compound of formula (1) in which $R_1$ is $C_1$–$C_4$ alkyl, —(CH$_2$)$_q$Ar$_2$, or —CH$_2$C(O)Ar$_2$. An appropriate alkylating agent is one which transfers a $C_1$–$C_4$ alkyl, —(CH$_2$)$_q$Ar$_2$, or —CH$_2$C(O)Ar$_2$, such as iodomethane, bromomethane, iodoethane, bromoethane, bromopropane, bromobutane, benzylbromide, benzylchloride, phenethylbromide, phenethylchloride, 3-chloro-1-phenyl-propane, 4-chloro-1-phenyl-butane, α-chloroacetophenone, α-bromoacetophenone, 3-[(chloro)acetyl]-indole, etc.

For example, a deprotection may involve a compound of formula (1) in which Ar$_1$ is benzyloxy substituted is deprotected to give a compound of formula (1) in which Ar$_1$ is hydroxy substituted. A compound of formula (1) in which Ar$_1$ has a benzyloxy substituent is contacted with trifluoroacetic acid. The reaction may be carried out using thioanisole as a solvent. The reaction is carried out at temperatures of between 0° C. and 60° C. The reaction require from 1 to 24 hours. The product can be isolated and purified by techniques well known in the art, such as evaporation, chromatography, and recrystallization.

For example, a modification may involve a compound of formula (1) is which $R_1$ is hydrogen is contacted with a slight molar excess of an appropriate alkylating agent. The reaction is carried out in the presence of a slight molar excess of a suitable base, such as sodium bicarbonate, potassium bicarbonate, diisopropylethyl amine or triethyl amine. The reaction is carried out in a suitable solvent, such as acetonitrile, dimethylformamide, ethanol, zylene, toluene, tetrahydrofuran, tetrahydrofuran/water mixtures, or dimethyl sulfoxide. The reaction may be carried out in the presence of a suitable catalyst, such as potassium iodide, sodium iodide, tetrabutylammonium iodide, trimethylbenzylammonium iodide, tetraethylammonium iodide, tetrabutylammonium bromide, trimethylbenzylammonium bromide, tetraethylammonium bromide, tetrabutylammonium hydrogen sulfate, trimethylbenzylammonium hydrogen sulfate, tetraethylammonium hydrogen sulfate, etc. The reaction is carried out at temperatures of from 20° C. to the reflux temperature of the solvent. The reaction generally requires from 1 to 48 hours. The product can be isolated and purified by techniques well known in the art, such as extraction, evaporation, chromatography, and recrystallization.

In Scheme A, optional step g, a compound of formula (1) in which $G_1$ is —C(O)— is reduced to give a compound of formula (1) in which $G_1$ is —CH$_2$—.

For example, a compound of formula (1) in which $G_1$ is —C(O)— is contacted with a suitable reducing agent, such as diisobutylaluminum hydride, borane, borane dimethylsulfide complex, or litium aluminumhydride with diisobutylaluminum hydride and borane dimethylsulfide complex being preferred. The reaction is carried out in a suitable solvent, such as tetrahydrofuran or toluene. The reaction is carried out at temperatures of from −20° C. to the refluxing temperature of the solvent. After an appropriate work-up, as is well known in the art, the work-up used depends on the products produced and the reducing reagent used, the product can be isolated and purified by techniques well known in the art, such as extraction, evaporation, chromatography, and recrystallization.

As is well known and appreciated in the art, Scheme A optional step f may be carried out after optional steps c, e or f as required to prepare the compounds of formula (1), and further, that Scheme A optional steps f and g may be carried out in any order which allows for the proper incorporation of groups as desired in the final product of formula (1).

The following examples and preparations present typical syntheses as described in Scheme A. These examples are understood to be illustrative only and are not intended to limit the scope of the invention in any way.

EXAMPLE 1

Synthesis of (R)-3-(1H-Indol-3-ylmethyl)-1-(2-phenyl-ethyl)-2-oxo-piperazine

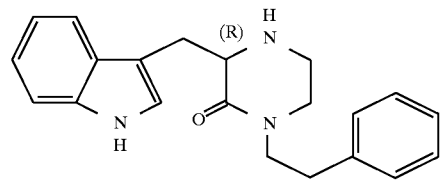

2-[(R)-2-(1H-Indol-3-yl)-1-carboxymethyl-ethylamino]-N-(t-butoxycarbonyl)-N-(2-phenyl-ethyl)-ethylamine Scheme A, step a Combine N-t-butoxycarbonyl-N-(2-oxo-ethyl)-2-phenyl-ethylamine (5.03 g, 19.0 mmol) and (R)-2-(1H-indol-3-yl)-1-carboxymethyl-ethylamine hydrochloride salt ((R)-tryptophan methyl ester hydrochloride salt) (4.9 g, 19.42 mmol) in methanol (50 mL) and stir for 30 minutes. Add sodium cyanoborohydride in solution (15.0 mL, 1M in THF, 15.0 mmol) and stir under an inert atmosphere for 16.5 hours. Concentrate in vacuo to obtain a residue. Dilute the residue with ethyl acetate and extract with water. Separate the layers, dry the organic layer over MgSO$_4$, filter, and evaporate in vacuo. Chromatograph on silica gel eluting with 50% ethyl acetate/hexane to give the title compound.

2-[(R)-2-(1H-Indol-3-yl)-1-carboxymethyl-ethylamino]-N-(2-phenyl-ethyl)-ethylamine hydrochloride disalt Scheme A, step b Combine 2-[(R)-2-(1H-Indol-3-yl)-1-carboxymethyl-ethylamino]-N-(t-butoxycarbonyl)-N-(2-phenyl-ethyl)- ethylamine (1.64 g, 3.53 mmol) and dichloromethane (30 mL). Slowly pass hydrogen chloride gas through the solution for 20 minutes. Stir for 1 hour. Add diethyl ether (150 mL) to form a solid. Filter and dry under vacuum to give the title compound. Elem. Anal. calculated for $C_{22}H_{27}N_3O_2.0.75$ $H_2O$: C, 58.70; H, 6.98; N, 9.14. Found: C, 58.71; H, 6.98; N, 9.14.

(R)-3-(1H-Indol-3-ylmethyl)-1-(2-phenyl-ethyl)-2-oxo-piperazine

Scheme A, optional step c

Dissolve 2-[(R)-2-(1H-Indol-3-yl)-1-carboxymethyl-ethylamino]-N-(2-phenyl-ethyl)-ethylamine hydrochloride disalt (3.80 g, 8.67 mmol) in toluene (40 mL). Add pyridine (20 mL) and heat to reflux for 23 hours. Cool to ambient temperature. Dilute the reaction with ethyl acetate and extract with water. Separate the layers, dry the organic layer over $MgSO_4$, filter, and evaporate in vacuo. Chromatograph on silica gel eluting sequentially with 50% ethyl acetate/hexane and 6% methanol/dichloromethane to give the title compound.

(R)-3-(1H-Indol-3-ylmethyl)-1-(2-phenyl-ethyl)-2-oxo-piperazine hydrochloride salt Dissolve (R)-3-(1H-Indol-3-ylmethyl)-1-(2-phenyl-ethyl)-2-oxo-piperazine (0.687 g, 1.50 mmol) in dichloromethane (20 mL). Cool to 0° C. Pass hydrochloride gas through the solution for 15 minutes. Evaporate in vacuo to obtain a residue. Dissolve the residue in hot ethanol (5 mL) and add diethyl ether. Cool and filter to give the title compound. Elem. Anal. calculated for $C_{21}H_{23}N_3O.HCl$: C, 68.19; H, 6.54; N, 11.36. Found: C, 67.79; H, 6.73; N, 11.20. Specific rotation $[\alpha]_D^{20}=+113°$ (c=1.00, DMSO).

EXAMPLE 2

Synthesis of (S)-3-(1H-Indol-3-ylmethyl)-1-(2-phenyl-ethyl)-2-oxo-piperazine

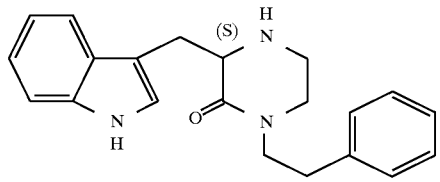

2-[(S)-2-(1H-Indol-3-yl)-1-carboxymethyl-ethylamino]-N-(t-butoxycarbonyl)-N-(2-phenyl-ethyl)-ethylamine Scheme A, step a Combine N-t-butoxycarbonyl-N-(2-oxo-ethyl)-2-phenyl-ethylamine (5.10 g, 19.16 mmol) and (S)-2-(1H-indol-3-yl)-1-carboxymethyl-ethylamine hydrochloride salt ((S)-tryptophan methyl ester hydrochloride salt) (4.90 g, 19.23 mmol) in methanol (50 mL) and stir for 10 minutes. Add sodium cyanoborohydride in solution (19.0 mL, 1M in THF, 19.0 mmol) and stir under an inert atmosphere for 18 hours. Concentrate in vacuo to obtain a residue. Dilute the residue with ethyl acetate and extract with water. Separate the layers, dry the organic layer over $MgSO_4$, filter, and evaporate in vacuo. Chromatograph on silica gel eluting with 50% ethyl acetate/hexane to give the title compound.

2-[(S)-2-(1H-Indol-3-yl)-1-carboxymethyl-ethylamino]-N-(2-phenyl-ethyl)-ethylamine hydrochloride disalt Scheme A, step b Combine 2-[(S)-2-(1H-Indol-3-yl)-1-carboxymethyl-ethylamino]-N-(t-butoxycarbonyl)-N-(2-phenyl-ethyl)-ethylamine (4.77 g, 10 mmol) and diethyl ether (50 mL). Cool to 0° C. in an ice-bath. Slowly pass hydrogen chloride gas through the solution for 30 minutes. Stir for 4 hour at 0° C. Warm to ambient temperature and stir for 1 hour. Evaporate in vacuo to give a residue. Dissolve the residue in methanol and triturate the residue with diethyl ether to form a solid. Filter and dry under vacuum to give the title compound. Elem. Anal. calculated for $C_{22}H_{27}N_3O_2.0.50$ $H_2O$: C, 59.06; H, 6.76; N, 9.39. Found: C, 58.90; H, 7.01; N, 9.18.

(S)-3-(1H-Indol-3-ylmethyl)-1-(2-phenyl-ethyl)-2-oxo-piperazine

Scheme A, optional step c

Dissolve 2-[(S)-2-(1H-Indol-3-yl)-1-carboxymethyl-ethylamino]-N-(2-phenyl-ethyl)-ethylamine hydrochloride disalt (3.12 g, 7.13 mmol) in toluene (40 mL). Add pyridine (20 mL) and heat to reflux for 15 hours. Cool to ambient temperature. Dilute the reaction with ethyl acetate and extract with water. Separate the layers, dry the organic layer over $MgSO_4$, filter, and evaporate in vacuo. Chromatograph on silica gel eluting sequentially with 50% ethyl acetate/hexane and 6% methanol/dichloromethane to give the title compound.

(S)-3-(1H-Indol-3-ylmethyl)-1-(2-phenyl-ethyl)-2-oxo-piperazine hydrochloride salt Dissolve (S)-3-(1H-Indol-3-ylmethyl)-1-(2-phenyl-ethyl)-2-oxo-piperazine (0.545 g, 1.64 mmol) in dichloromethane (20 mL). Cool to 0° C. Pass hydrochloride gas through the solution for 15 minutes. Evaporate in vacuo to obtain a residue. Triturate with diethyl ether to give a solid. Filter and dry in vacuo to give the title compound. Elem. Anal. calculated for $C_{21}H_{23}N_3O.HCl.0.8$ $H_2O$: C, 65.74; H, 6.70; N, 10.95. Found: C, 66.14; H, 6.96; N, 10.57. Specific rotation $[\alpha]_D^{20}=-104°$ (c=1.00, DMSO).

EXAMPLE 3

Synthesis of (R)-3-(1H-Indol-3-ylmethyl)-1-[2-[4-(benzyloxy)phenyl]ethyl]-2-oxo-piperazine

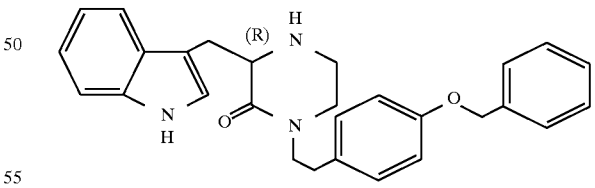

2-[(R)-2-(1H-Indol-3-yl)-1-carboxymethyl-ethylamino]-N-(t-butoxycarbonyl)-N-[2-[(4-benzyloxy)phenyl-ethyl]]-ethylamine Scheme A, step a Combine N-t-butoxycarbonyl-N-(2-oxo-ethyl)-2-[4-benzyloxy)phenyl]-ethylamine (8.31 g, 22.49 mmol) and (R)-2-(1H-indol-3-yl)-1-carboxymethyl-ethylamine hydrochloride salt ((R)-tryptophan hydrochloride salt) (5.46 g, 21.44 mmol) in methanol (100 mL) and stir for 30 minutes. Add sodium cyanoborohydride in solution (19.0 mL, 1M in THF, 19.0 mmol) and stir under an inert atmosphere for 24 hours. Concentrate in vacuo to obtain a residue. Dilute the residue with ethyl acetate and extract with water. Separate the layers, dry the organic layer over MgSO$_4$, filter, and evaporate in vacuo. Chromatograph on silica gel eluting sequentially with 30% ethyl acetate/hexane and 50% ethyl acetate/hexane to give the title compound: R$_f$=0.55 (silica gel, 70% ethyl acetate/hexane). HRMS calculated for C$_{28}$H$_{29}$N$_3$O$_2$ 572.3124. Found 572.3109.

2-[(R)-2-(1H-Indol-3-yl)-1-carboxymethyl-ethylamino]-N-[2-[(4-benzyloxy)phenyl-ethyl]]-ethylamine hydrochloride disalt Scheme A, step b Combine 2-[(R)-2-(1H-indol-3-yl)-1-carboxymethyl-ethylamino]-N-(t-butoxycarbonyl)-N-[2-[(4-benzyloxy)phenyl-ethyl]]-ethylamine (6.00 g, 10.5 mmol) and 4M hydrochloric acid in dioxane (40 mL). Allow to stir for 1 hour. Evaporate in vacuo to give the title compound.

(R)-3-(1H-Indol-3-ylmethyl)-1-[2-[4-(benzyloxy)phenyl]ethyl]-2-oxo-piperazine

Scheme A, optional step c

Dissolve 2-[(R)-2-(1H-Indol-3-yl)-1-carboxymethyl-ethylamino]-N-[2-[(4-benzyloxy)phenyl-ethyl]]-ethylamine hydrochloride disalt (5.49 g, 10.08 mmol) in toluene (60 mL). Add pyridine (30 mL) and heat to reflux for 16 hours. Cool to ambient temperature. Dilute the reaction with ethyl acetate and extract with water. Separate the layers, dry the organic layer over MgSO$_4$, filter, and evaporate in vacuo. Chromatograph on silica gel eluting sequentially with 50% ethyl acetate/hexane and 6% methanol/dichloromethane to give the title compound: TLC R$_f$=0.44 (silica gel, 10% methanol/dichloromethane). Elem. Anal. calculated for C$_{28}$H$_{29}$N$_3$O$_2$.0.25 H$_2$O: C, 75.74; H, 6.70; N, 9.46. Found: C, 75.54; H, 6.55; N, 9.32.

EXAMPLE 4

Synthesis of (S)-3-(1H-Indol-3-ylmethyl)-1-[2-[4-(benzyloxy)phenyl]ethyl]-2-oxo-piperazine

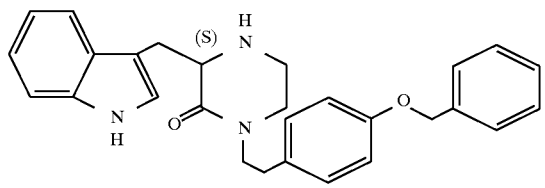

2-[(S)-2-(1H-Indol-3-yl)-1-carboxymethyl-ethylamino]-N-(t-butoxycarbonyl)-N-[2-[(4-benzyloxy)phenyl-ethyl]]-ethylamine Scheme A, step a Combine N-t-butoxycarbonyl-N-(2-oxo-ethyl)-2-[4-benzyloxy)phenyl]-ethylamine (0.37 g, 1.0 mmol) and (S)-2-(1H-indol-3-yl)-1-carboxymethyl-ethylamine hydrochloride salt ((S)-tryptophan hydrochloride salt) (0.25 g, 1.0 mmol) in methanol (10 mL) and stir for 5 minutes. Add sodium cyanoborohydride in solution (0.8 mL, 1M in THF, 0.8 mmol) and stir under an inert atmosphere for 24 hours. Concentrate in vacuo to obtain a residue. Dilute the residue with ethyl acetate and extract with water. Separate the layers, dry the organic layer over MgSO$_4$, filter, and evaporate in vacuo. Chromatograph on silica gel eluting with 5% methanol/dichloromethane to give the title compound: TLC R$_f$=0.62 (silica gel, 10% methanol/dichloromethane).

2-[(S)-2-(1H-Indol-3-yl)-1-carboxymethyl-ethylamino]-N-[2-[(4-benzyloxy)phenyl-ethyl]]-ethylamine hydrochloride disalt Scheme A, step b Combine 2-[(S)-2-(1H-indol-3-yl)-1-carboxymethyl-ethylamino]-N-(t-butoxycarbonyl)-N-[2-[(4-benzyloxy)phenyl-ethyl]]-ethylamine (2.1 g, 3.67 mmol)and 4M hydrochloric acid in dioxane (20 mL). Allow to stir for 1 hour. Evaporate in vacuo to give the title compound as a solid: TLC R$_f$=0.54 (silica gel, 85% chloroform, 10% methanol, 5% acetic acid).

(S)-3-(1H-Indol-3-ylmethyl)-1-[2-[4-(benzyloxy)phenyl]ethyl]-2-oxo-piperazine

Scheme A, optional step c

Dissolve 2-[(S)-2-(1H-Indol-3-yl)-1-carboxymethyl-ethylamino]-N-[2-[(4-benzyloxy)phenyl-ethyl]]-ethylamine hydrochloride disalt (1.94 g, 3.56 mmol) in toluene (33 mL). Add pyridine (11 mL) and heat to reflux for 16 hours. Cool to ambient temperature. Dilute the reaction with ethyl acetate and extract with water. Separate the layers, dry the organic layer over MgSO$_4$, filter, and evaporate in vacuo. Chromatograph on silica gel eluting sequentially with 50% ethyl acetate/hexane and 5% methanol/dichloromethane to give the title compound as a white solid: TLC R$_f$=0.42 (silica gel, 10% methanol/dichloromethane). Elem. Anal. calculated for C$_{28}$H$_{29}$N$_3$O$_2$.0.25 H$_2$O; C, 75.74; H, 6.70; N, 9.46. Found: C, 75.82; H. 6.66; N, 9.49.

EXAMPLE 5

Synthesis of (R)-3-(1H-Indol-3-ylmethyl)-1-(2,2-bis-phenyl-ethyl)-2-oxo-piperazine

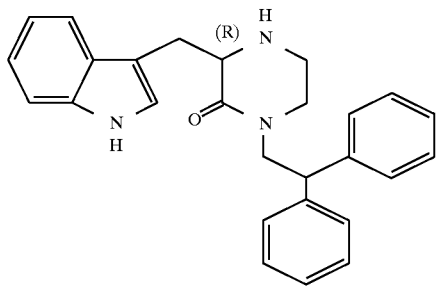

2-[(R)-2-(1H-Indol-3-yl)-1-carboxymethyl-ethylamino]-N-(t-butoxycarbonyl)-N-(2,2-bis-phenyl-ethyl)]-ethylamine Scheme A, step a Combine N-t-butoxycarbonyl-N-(2-oxo-ethyl)-2,2-bis-phenyl]-ethylamine (0.22 g, 0.69 mmol) and (R)-2-(1H-indol-3-yl)-1-carboxymethyl-ethylamine hydrochloride salt ((R)-tryptophan methyl ester hydrochloride salt) (0.20 g, 0.79 mmol) in methanol and stir for 10 minutes. Add sodium cyanoborohydride in solution (0.55 mL, 1M in THF, 0.55 mmol) and stir under an inert atmosphere for 24 hours. Concentrate in vacuo to obtain a residue. Dilute the residue with ethyl acetate and extract with water. Separate the layers, dry the organic layer over MgSO$_4$, filter, and evaporate in vacuo. Chromatograph on silica gel eluting with 50% ethyl acetate/hexane to give the title compound.

2-[(R)-2-(1H-Indol-3-yl)-1-carboxymethyl-ethylamino]-N-(2,2-bis-phenyl-ethyl)]-ethylamine Scheme A, step b Combine 2-[(R)-2-(1H-indol-3-yl)-1-carboxymethyl-ethylamino]-N-(t-butoxycarbonyl)-N-(2,2-bis-phenyl-ethyl)

]-ethylamine (0.22 g, 0.41 mmol) and dichloromethane (5 mL). Slowly pass hydrogen chloride gas through the solution for 30 minutes. Stir for 1 hour. Evaporate in vacuo to give a residue. Triturate the residue with diethyl ether and evaporate in vacuo to give a residue. Dry under vacuum to give the title compound.

(R)-3-(1H-Indol-3-ylmethyl)-1-(2,2-bis-phenyl-ethyl)-2-oxo-piperazine

Scheme A, optional step c

Combine 2-[(R)-2-(1H-indol-3-yl)-1-carboxymethyl-ethylamino]-N-(2,2-bis-phenyl-ethyl)]-ethylamine (0.16 g, 0.31 mmol) and toluene (5 mL). Add pyridine (2.5 mL) and heat to reflux for 16 hours. Cool to ambient temperature. Concentrate the reaction mixture in vacuo to obtain a residue. Dilute the residue with ethyl acetate and extract with water. Separate the layers, dry the organic layer over $MgSO_4$, filter, and evaporate in vacuo. Chromatograph on silica gel eluting with 6% methanol/dichloromethane to give the title compound: TLC $R_f$=0.37 (silica gel, 6% methanol/dichloromethane.

EXAMPLE 6

Synthesis of (R)-3-(1H-Indol-3-ylmethyl)-1-[2-[4-(hydroxy)phenyl]ethyl]]-2-oxo-piperazine

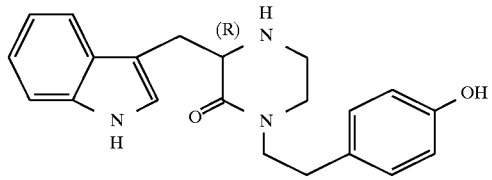

(R)-3-(1H-Indol-3-ylmethyl)-1-[2-[4-(hydroxy)phenyl]ethyl]]-2-oxo-piperazine

Scheme A, optional deprotection step f

Combine (R)-3-(1H-Indol-3-ylmethyl)-1-[2-[4-(benzyloxy)phenyl]ethyl]-2-oxo-piperazine (0.6 g, 1.36 mmol), thioanisole (8 mL), and trifluoroacetic acid (27 mL). Stir at ambient temperature for 1 hour. Concentrate in vacuo. Chromatograph on silica gel eluting 5% methanol/dichloromethane to give the title compound: TLC $R_f$=0.39 (silica gel, 10% methanol/dichloromethane). Elem. Anal. calculated for $C_{21}H_{23}N_3O_2 \cdot 0.75$ $H_2O$: C, 69.50; H, 6.80; N, 11.58. Found: C, 69.64; H, 6.81; N, 11.52.

EXAMPLE 7

Synthesis of (S)-3-(1H-Indol-3-ylmethyl)-1-[2-[4-(hydroxy)phenyl]ethyl]-2-oxo-piperazine

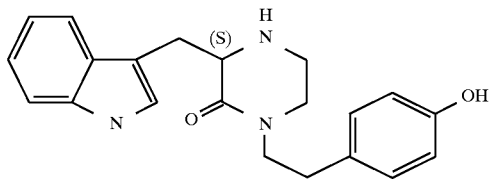

(S)-3-(1H-Indol-3-ylmethyl)-1-[2-[4-(hydroxy)phenyl]ethyl]-2-oxo-piperazine

Scheme A, optional deprotection step f

Combine (S)-3-(1H-Indol-3-ylmethyl)-1-[2-[4-(benzyloxy)phenyl]ethyl]-2-oxo-piperazine (0.13 g, 0.3 mmol), thioanisole (1.76 mL), and trifluoroacetic acid (6 mL). Stir at ambient temperature for 1 hour. Concentrate in vacuo. Chromatograph on silica gel eluting sequentially with 3% methanol/dichloromethane and 5% methanol/dichloromethane to give the title compound: TLC $R_f$=0.49 (silica gel, 10% methanol/dichloromethane). HRMS calculated for $C_{21}H_{23}N_3O_2$ 349.1790. Found 349.1790.

PREPARATION 1

Synthesis of 3-[(chloro)acetyl]-indole

According to the method of J. Bergman et al. *Tet.* 29, 971–976 (1973), combine indole (11.7 g, 100 mmol), pyridine (8.1 mL, 100 mmol), and toluene (250 mL). Heat to 55° C. Add dropwise a solution of chloroacetyl chloride (8 mL, 100 mmol) in toluene (10 mL). After 2 hours, cool to ambient temperature. Dilute the reaction mixture with ethyl acetate and extract with water. Dry the organic layer over $MgSO_4$, filter and evaporate in vacuo to give a residue. Recrystallize the residue from ethanol to give the title compound.

EXAMPLE 8

Synthesis of (R)-3-(1H-Indol-3-ylmethyl)-4-[2-(1H-indol-3-yl)-2-oxo-ethyl]-1-(2-phenyl-ethyl)-2-oxo-piperazine

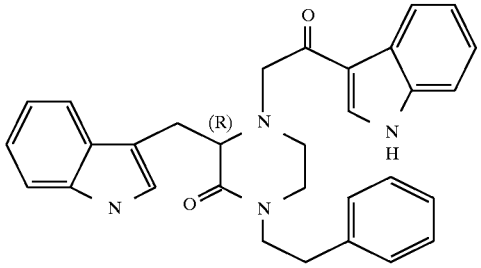

(R)-3-(1H-Indol-3-ylmethyl)-4-[2-(1H-indol-3-yl)-2-oxo-ethyl]-1-(2-phenyl-ethyl)-2-oxo-piperazine Scheme A, optional modification step f Dissolve (R)-3-(1H-indol-3-ylmethyl)-1-(2-phenyl-ethyl)-2-oxo-piperazine (0.50 g, 1.50 mmol) in acetonitrile (15 mL). Add 3-[(chloro)acetyl]-indole (0.33 g, 1.70 mmol), potassium bicarbonate (0.60 g, 6.0 mmol), and tetrabutylammonium iodide (0.060 g, 0.16 mmol). Heat to reflux for 2 hours. Evaporate in vacuo to obtain a residue. Dissolve the residue in ethyl acetate and extract with water. Dry the organic layer over $MgSO_4$, filter, and evaporate in vacuo to give a residue. Chromatograph on silica gel eluting sequentially with 50% ethyl acetate/hexane and 6% methanol/dichloromethane. Recrystallize from chloroform to give the title compound was a solid: TLC $R_f$=0.55 (silica gel, 10% methanol/dichloromethane). Elem. Anal. calculated for $C_{31}H_{30}N_4O_2$: C, 75.89; H, 6.16; N, 11.42. Found: C, 75.37; H, 6.27; N, 11.12. HRMS calculated (M+H) 491.2447. Found 491.2447.

EXAMPLE 9

Synthesis of (R)-3-(1H-Indol-3-ylmethyl)-4-[2-(1H-indol-3-yl)-2-oxo-ethyl]-1-(2,2-bis-phenyl-ethyl)-2-oxo-piperazine

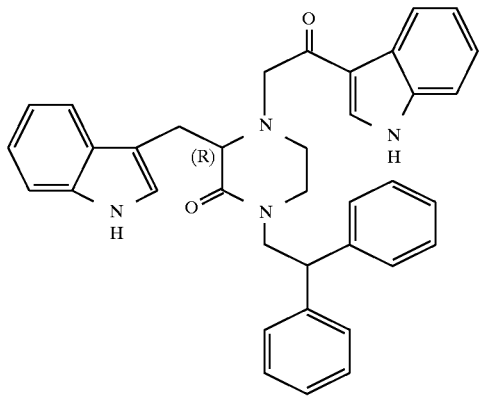

(R)-3-(1H-Indol-3-ylmethyl)-4-[2-(1H-indol-3-yl)-2-oxo-ethyl]-1-(2,2-bis-phenyl-ethyl)-2-oxo-piperazine
Scheme A, optional modification step f Dissolve (R)-3-(1H-indol-3-ylmethyl)-1-(2,2-bis-phenyl-ethyl)-2-oxo-piperazine (0.50 g, 1.22 mmol) in acetonitrile (15 mL). Add 3-[(chloro)acetyl]-indole (0.26 g, 1.34 mmol), potassium bicarbonate (0.50 g, 5.0 mmol), and tetrabutylammoniun iodide (0.055 g, 0.15 mmol). Heat to reflux for 2 hours. Evaporate in vacuo to obtain a residue. Dissolve the residue in ethyl acetate and extract with water. Dry the organic layer over MgSO$_4$, filter, and evaporate in vacuo to give a residue. Chromatograph on silica gel eluting with 50% ethyl acetate/hexane. Recrystallize from chloroform to give the title compound as a solid. HRMS calculated for C$_{36}$H$_{34}$N$_4$O$_2$ 567.2760. Found 567.2733.

EXAMPLE 10

Synthesis of (R)-3-(1H-Indol-3-ylmethyl)-4-[2-(1H-indol-3-yl)-2-oxo-ethyl]-1-[2-[4-(benzyloxy)phenyl]ethyl]-2-oxo-piperazine

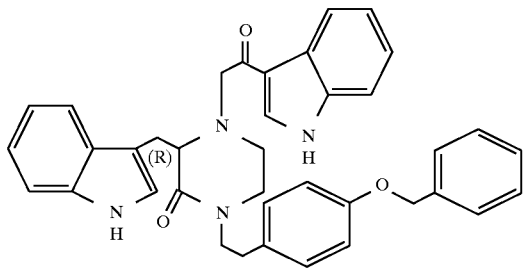

(R)-3-(1H-Indol-3-ylmethyl)-4-[2-(1H-indol-3-yl)-2-oxo-ethyl]-1-[2-[4-(benzyloxy)phenyl]ethyl]-2-oxo-piperazine
Scheme A, optional modification step f Combine (R)-3-(1H-indol-3-ylmethyl)-4-[2-(1H-indol-3-yl)-2-oxo-ethyl]-1-[2-[4-(benzyloxy)phenyl]ethyl]-2-oxo-piperazine (0.67 g, 1.53 mmol), 3-[(chloro)acetyl]-indole (0.31 g, 1.63 mmol), and diisopropylethylamine (0.31 mL, 1.84 mmol) in acetonitrile (30 mL). Heat to reflux for 16 hours. Evaporate in vacuo. Chromatograph on silica gel eluting sequentially with 50% ethyl acetate/hexane and 3% methanol/dichloromethane. Recrystallize from chloroform to give the title compound as a white solid: TLC R$_f$=0.67 (silica gel, 10% methanol/dichloromethane); mp; 175°–176° C. Elem. Anal. calculated for C$_{31}$H$_{30}$N$_4$O$_2$.0.25H$_2$O: C, 75.20; H, 6.21; N, 11.32. Found: C, 75.20; H, 6.16; N, 11.33.

EXAMPLE 11

Synthesis of (R)-3-(1H-Indol-3-ylmethyl)-4-[2-(1H-indol-3-yl)-2-oxo-ethyl]-1-[2-[4-(hydroxy)phenyl)ethyl]-2-oxo-piperazine

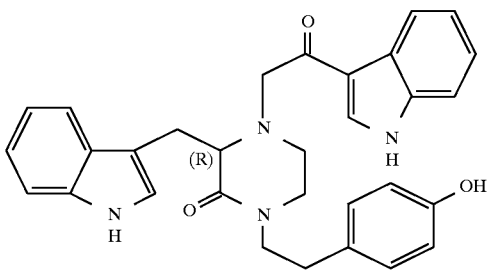

(R)-3-(1H-Indol-3-ylmethyl)-4-[2-(1H-indol-3-yl)-2-oxo-ethyl]-1-[2-[4-(hydroxy)phenyl]ethyl]-2-oxo-piperazine
Scheme A, optional deprotection step f Combine (R)-3,4-bis-(1H-indol-3-ylmethyl)-4-[2-(1H-indol-3-yl)-2-oxo-ethyl]-1-[2-[4-(benzyloxy)phenyl]ethyl]-2-oxo-piperazine (0.19 g, 0.32 mmol), thioanisole (1.90 mL), and trifluoroacetic acid (6 mL). Stir at ambient temperature for 1 hour. Concentrate in vacuo. Chromatograph on silica gel eluting with 5% methanol/dichloromethane to give the title compound: TLC R$_f$=0.57 (silica gel, 10% methanol/dichloromethane. HRMS calculated for C$_{30}$H$_{30}$N$_4$O$_3$ 507.2396. Found 507.2392.

EXAMPLE 12

Synthesis of (R)-3-(1H-Indol-3-ylmethyl)-4-[(S)-pyroglutamoyl]-1-(2-phenyl-ethyl)-2-oxo-piperazine

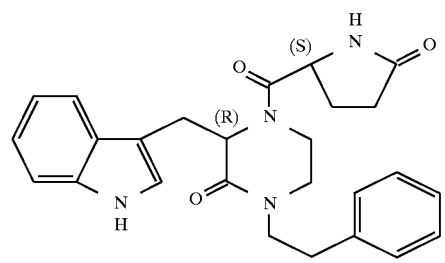

(R)-3-(1H-Indol-3-ylmethyl)-4-[(S)-pyroglutamoyl]-2-oxo-ethyl]-1-(2-phenyl-ethyl)-2-oxo-piperazine
Scheme A, optional modification step f Dissolve (R)-3-(1H-indol-3-ylmethyl)-1-(2-phenyl-ethyl)-2-oxo-piperazine (0.50 g, 1.50 mmol) in dimethylformamide (15 mL). Add (S)-pyroglutamic acid (0.22 g, 1.67 mmol), 1-(3-dimethyl aminopropyl)-3-ethylcarbodiimide hydrochloride (0.32 g, 1.67 mmol), and 1-hydroxybenzotriazole hydrate (0.23 g, 1.67 mmol). After 24 hours, pour the reaction mixture into ethyl acetate. Extract with water and saturated aqueous sodium chloride solution. Dry the organic layer over MgSO$_4$, filter, and evaporate in vacuo to give a residue. Chromatograph the residue on silica gel eluting with 6% methanol/ dichloromethane to give a residue. Recrystallize the residue obtained by chromatography from ethanol to give the title compound. Elem Anal. calculated for $C_{26}H_{28}N_4O_3 \cdot 0.25H_2O$: C, 69.55; H, 6.40; N, 12.48. Found: C, 69.46, H, 6.48; N, 12.75.

EXAMPLE 13

Synthesis of (R)-3-(1H-Indol-3-ylmethyl)-4-[2-phenyl-2-oxo-ethyl]-1-(2-phenyl-ethyl)-2-oxo-piperazine

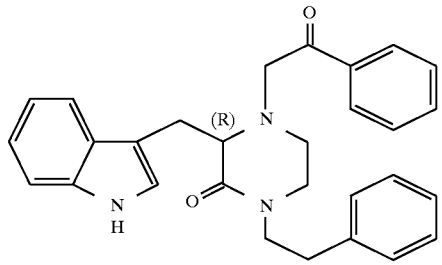

(R)-3-(1H-Indol-3-ylmethyl)-4-[2-phenyl-2-oxo-ethyl]-1-(2-phenyl-ethyl)-2-oxo-piperazine Scheme A, optional modification step f Prepare by a method similar to Example 8 using (R)-3-(1H-indol-3-ylmethyl)-1-(2-phenyl-ethyl)-2-oxo-piperazine and α-chloroacetophenone to give the title compound.

EXAMPLE 14

Synthesis of (R)-3-(1H-Indol-3-ylmethyl)-4-[(phenyl)methyl]-1-(2-phenyl-ethyl)-2-oxo-piperazine

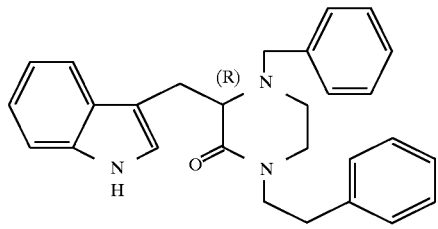

(R)-3-(1H-Indol-3-ylmethyl)-4-((phenyl)methyl]-1-(2-phenyl-ethyl)-2-oxo-piperazine Scheme A, optional modification step f Dissolve (R)-3-(1H-indol-3-ylmethyl)-1-(2-phenyl-ethyl)-2-oxo-piperazine (0.50 g, 1.50 mmol) in tetrahydrofuran (15 mL). Add benzyl bromide (1.70 mmol), and potassium carbonate (6.0 mmol). Heat to reflux for 24 hours. Evaporate in vacuo to obtain a residue. Dissolve the residue in ethyl acetate and extract with water. Dry the organic layer over $MgSO_4$, filter, and evaporate in vacuo to give a residue. Chromatograph on silica gel to give the title compound

EXAMPLE 15

Synthesis of (S)-3-(1H-Indol-3-ylmethyl)-1-(2-phenyl-ethyl)-piperazine

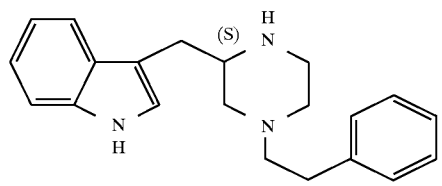

(S)-3-(1H-Indol-3-ylmethyl)-1-(2-phenyl-ethyl)-piperazine

Scheme A, step a

Combine lithiium aluminumhydride (100 mmol) and tetrahydrofuran (75 ml). Add (S)-3-(1H-Indol-3-ylmethyl)-1-(2-phenyl-ethyl)-2-oxo-piperazine (25 mmol) portionwise. Heat to reflux. After 24 hours, cool to ambient temperature. Carefully add water (3.8 mL), 15% aqueous sodium hydroxide solution (3.8 mL), and water (10.5 mL). Stir vigourously for 1 hour. Filter, rinse the filter cake repeatedly with tetrahydrofuran. Concentrate the filtrate in vacuo to obtain a residue. Chromatograph the residue to give the title compound.

A general synthetic procedure is set forth in Scheme B for preparing the aldehydes of formula (4). The reagents and starting materials are readily available to one of ordinary skill in the art. In Scheme B, all substituents, unless otherwise indicated, are as previously defined.

SCHEME B

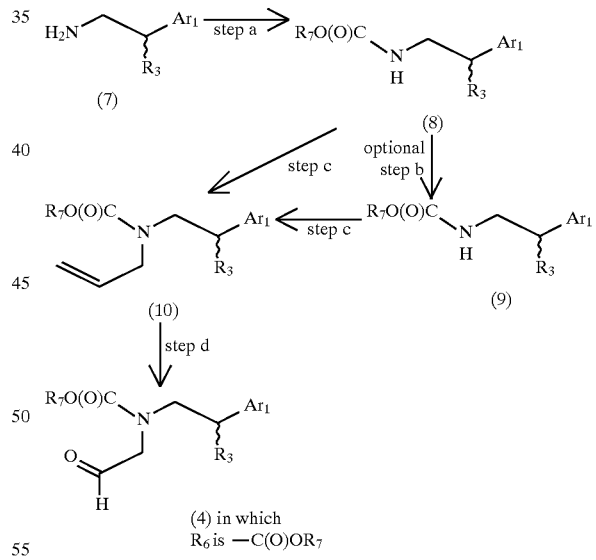

(4) in which
$R_6$ is $-C(O)OR_7$

In Scheme B, step a, an appropriate arylethylamine of structure (7) or salt thereof is protected with a suitable carbamate forming reagent to give a carbamate protected arylethylamine of structure (8).

An appropriate arylethylamine of structure (7) is one in which $Ar_1$ and $R_3$ are as desired in the final compound of formula (1), or can be deprotected to give a $Ar_1$ and $R_3$ as desired in the final compound of formula (1).

For example, an appropriate arylethylamine of structure (7) or a salt thereof is contacted with a suitable carbamate forming reagent, such as methyl chloroformate, ethylchloroformate, benzyl chloroformate, di-t-butyl dicarbonate, etc. When a salt appropriate arylethylamine of structure (7) is used the reaction is carried out in the presence of an equimolar amount of a suitable base, such as triethylamine, N-methylmorpholine, or diisopropylethylamine. The reaction is carried out in a suitable solvent, such as tetrahydrofuran, dimethylformamide, ethyl acetate, or dimethylformamide/ethyl acetate mixtures. The reactions are generally carried out at ambient temperature. The product can be isolated and purified by techniques well known in the art, such as extraction, evaporation, chromatography, and recrystallization.

In Scheme B, optional step b, a substituent on $R_3$ or $Ar_1$ of a carbamate protected arylethylamine of structure (8) may be converted to a group as is desired in the final product of formula (1) to give a carbamate arylethylamine of structure (9).

For example, a carbamate protected arylethylamine of structure (8) in which $Ar_1$ has a hydroxy substituent is contacted with a suitable alkylating reagent, such as iodomethane, bromoethane, bromopropane, chloropropane, bromobutane, chlorobutane, benzyl bromide, benzyl chloride, 4-methoxybenzyl chloride, etc. The reaction is carried out in a suitable solvent, such as tetrahydrofuran, dimethylformamide, or dichloromethane. The reaction is carried out in the presence of a suitable base, such as triethylamine, sodium carbonate, or diisopropylethylamine. The reactions are generally carried out at ambient temperature and generally requires form 1 to 48 hours. The product can be isolated and purified by techniques well known in the art, such as extraction, evaporation, chromatography, and recrystallization.

Alternately, such a reaction may be carried out under phase transfer catalysis, using a suitable catalyst, such as tetrabutylammonium bromide, tetraethylammonium chloride, or tetrabutylammonium hydrogen sulfate, tetraethylammonium bromide, trimethylbenzylammonium bromide, etc. The reaction is carried out in a suitable solvent system, such as dichloromethane/water, toluene/water, or ethyl acetate water. The two-phase reaction is carried out in the presence of a suitable base, such as sodium hydroxide or potassium hydroxide. The reactions are carried out at ambient temperature. The reaction generally requires form 1 to 48 hours. The product can be isolated and purified by techniques well known in the art, such as extraction, evaporation, chromatography, and recrystallization.

In Scheme B, step c, a carbamate protected arylethylamine of structure (9) is allylated to give a carbamate protected allylamine of structure (10).

For example, a carbamate protected arylethylamine of structure (9) is contacted with an excess of allyl bromide or allyl chloride. The reaction is carried out in the presence of a suitable base, such as sodium hydride, n-butyllithium, or lithium diisopropylamide. The reaction is carried out in a suitable solvent, such as tetrahydrofuran, dimethylformamide, or tetrahydrofuran/dimethylformamide mixtures. The reaction is carried out at temperature of from 0° C. to the reflux temperature of the solvent. The reaction may require additional allyl bromide or allyl chloride after 1 to 24 hours in order to increase the yield of allylated product. The reaction generally requires from 12 to 72 hours. The product can be isolated and purified by techniques well known in the art, such as extraction, evaporation, chromatography, and recrystallization.

In Scheme B, step d, a carbamate protected allylamine of structure (10) is converted to an aldehyde of structure (4). A carbamate protected allylamine of structure (10) may be converted to an aldehyde of structure (4) by either; ozonolysis in the presence of methanol followed by a reductive work-up, or an osmium tetraoxide mediated formation of an intermediate diol followed by oxidative cleavage with lead tetraacetate.

For example, a carbamate protected allylamine of structure (10) is contacted with ozone in the presence of methanol. The reaction is carried out in a suitable solvent, such as dichloromethane. The reaction is carried out a at temperature of from about −100° C. to about −60° C., with about −70° C. being preferred. The reaction is worked-up reductively by the addition of a suitable reducing agent, such as tributylphosphine or dimethylsulfide. The product may be isolated by evaporation and may be used without further purification. The product may be purified by techniques well known in the art, such as chromatography and recrystallization.

Alternatively, for example, a carbamate protected allylamine of structure (10) is contacted with osmium tetraoxide to give an intermediate diol. The reaction may be carried out using a 0.01 to 0.05 molar equivalents of osmium tetraoxide and a slight molar excess of an oxidant, such as N-methylmorpholine-N-oxide or sodium meta-periodate. The reaction is carried out in a solvent, such as acetone/water mixtures. The reaction is carried out at ambient temperature and generally requires from 12 to 48 hours. The reaction mixture is added to a saturated solution of sodium bisulfite or sodium thiosulfate and the intermediate diol is isolated by extraction and evaporation and used without further purifications. The intermediate dial is contacted with a slight molar excess of lead tetraacetate. The lead tetraacetate reaction is carried out in a solvent, such as chloroform. The reaction is generally carried out at ambient temperature and generally requires from 30 minutes to 8 hours. The product may be isolated by extraction and evaporation and may be used without further purification. The product may be purified by techniques well known in the art, such as chromatography and recrystallization.

The following examples and preparations present typical syntheses as described in Scheme B. These preparations are understood to be illustrative only and are not intended to limit the scope of the invention in any way.

PREPARATION 2

Synthesis of N-t-Butoxycarbonyl-N-(2-oxo-ethyl)-2-phenyl-ethylamine

N-t-Butoxycarbonyl-2-phenyl-ethylamine
Scheme B, step a

Combine phenethylamine hydrochloride (15.8 g, 100 mmol) and N-methylmorpholine (11 mL, 100 mmol) in dichloromethane (100 mL). Cool to 0° C. Add dimethylaminopyridine (1.0 g, 8.2 mmol) and di-t-butyl dicarbonate (22.0 g, 100 mmol) and allow to stir at 0° C. for 1 hour. Warm to ambient temperature and stir for 18 hours. Evaporate in vacuo to give a residue. Dilute the residue with ethyl acetate and extract with water. Dry the organic layer over $MgSO_4$, filter, and evaporate in vacuo to give the title compound.

N-t-Butoxycarbonyl-N-allyl-2-phenyl-ethylamine
Scheme B, step c

Combine N-t-butoxycarbonyl-2-phenyl-ethylamine (22.1 g, 100 mmol) and THF (100 mL) under an inert atmosphere. Cool to 0° C. in an ice-bath. Add portionwise sodium hydride (0.206 g, 110 mmol) and allow to stir until hydrogen evolution ceases. Add allyl bromide (9.50 mL, 110 mmol)

and warm to ambient temperature. Cool again to 0° C. in an ice-bath. Add sodium hydride (0.92 g, 40 mmol) and allow to stir until hydrogen evolution ceases. Add allyl bromide (3.0 mL, 35.0 mmol) and heat to reflux for 18 hours. Cool to ambient temperature. Add a saturated aqueous solution of ammonium chloride (200 mL) and extract with ethyl acetate. Dry the organic layer over $MgSO_4$, filter, and evaporate in vacuo. Chromatograph eluting sequentially with hexane and 10% ethyl acetate/hexane to give the title compound.

N-t-Butoxycarbonyl-N-(2-oxo-ethyl)-2-phenyl-ethylamine

Scheme B, step d

Dissolve N-t-butoxycarbonyl-N-allyl-2-phenyl-ethylamine (7.88 g, 21.44 mmol) in dichloromethane (200 mL) and methanol (5 mL). Cool to −78° C. Pass ozonized oxygen through the solution until a persistent light blue color is obtained. Pass nitrogen through the solution until the blue color dissipates. Add dimethyl sulfide (20 mL). Allow the reaction mixture to warm to ambient temperature and stir for 5 hours. Concentrate in vacuo to obtain a residue. Dilute the residue with ethyl acetate and extract with water. Separate the layers, dry the organic layer over $MgSO_4$, filter, and evaporate in vacuo to give the title compound.

PREPARATION 3

Synthesis of N-t-Butoxycarbonyl-N-(2-oxo-ethyl)-2-[(4-benzyloxy)-phenyl]-ethylamine N-t-Butoxycarbonyl-2-[(4-hydroxy-phenyl)]-ethylamine Scheme B, step a Combine 2-[(4-hydroxy)-phenyl]-ethylamine hydrochloride (3.47 g, 20.0 mmol), diisopropylethylamine (3.48 mL, 20.0 mmol), and di-t-butyl dicarbonate (4.36 g, 20.0 mmol) in 1/1 DMF/ethyl acetate (40 mL). Stir at ambient temperature for 2 hours. Dilute with ethyl acetate and extract with water. Dry the organic layer over $MgSO_4$, filter, and evaporate in vacuo to give the title compound: TLC $R_f$=0.32 (silica gel, 30% ethyl acetate/hexane).

N-t-Butoxycarbonyl-2-[(4-benzyloxy)-phenyl]-ethylamine

Scheme B, optional step b

Combine N-t-butoxycarbonyl-2-[(4-hydroxy)-phenyl]-ethylamine (2.93 g, 12.34 mmol), sodium hydroxide (0.99 g, 24.7 mmol), tetrabutylammonium bromide (0.397 g, 1.23 mmol), and benzyl bromide (1.48 g, 12.3 mmol) in water (60 mL) and dichloromethane (60 mL). Stir for 20 hours. Add sodium hydroxide (0.99 g, 24.7 mmol) water (40 mL) and benzyl bromide (0.71 g, 6.2 mmol) and stir for 5 hours. Add benzyl bromide (0.71 g, 6.2 mmol) and stir for 20 hours more. Extract the reaction mixture with water. Dry the organic layer over $MgSO_4$, filter, and evaporate in vacuo. Chromatograph eluting sequentially hexane and 10% ethyl acetate/hexane to give the title compound as an oil.

N-t-Butoxycarbonyl-N-allyl-2-[(4-benzyloxy)-phenyl]-ethylamine

Scheme B, step c

Combine N-t-butoxycarbonyl-2-(4-benzyloxy-phenyl)-ethylamine (1.27 g, 3.90 mmol) and DMF (8 mL) and THF (70 mL) under an inert atmosphere. Cool to 0° C. in an ice-bath. Add sodium hydride (0.206 g, 8.58 mmol) and allow to stir until hydrogen evolution ceases. Add allyl bromide (2.02 mL, 23.4 mmol) and heat to reflux. Cool again to 0° C. in an ice-bath. Add sodium hydride (0.10 g, 4.4 mmol) and allow to stir until hydrogen evolution ceases. Add allyl bromide (1.0 mL, 12.7 mmol) and heat to reflux. Add a saturated aqueous solution of ammonium chloride (200 mL) and extract with dichloromethane. Dry the organic layer over $MgSO_4$, filter, and evaporate in vacuo. Chromatograph eluting sequentially with hexane and 10% ethyl acetate/hexane to give the title compound. $R_f$=0.72 (silica gel, 30% ethyl acetate/hexane)

N-t-Butoxycarbonyl-N-(2-oxo-ethyl)-2-[(4-benzyloxy)-phenyl]-ethylamine

Scheme B, step d

Dissolve N-t-butoxycarbonyl-N-allyl-2-[(4-benzyloxy)-phenyl]-ethylamine (7.88 g, 21.44 mmol) in dichloromethane (180 mL) and methanol (20 mL) containing pyridine (0.08 mL). Cool to −78° C. Pass ozonized oxygen through the solution until a persistent light blue color is obtained. Pass nitrogen through the solution until the blue color dissipates. Add dimethyl sulfide (34 mL). Allow the reaction mixture to warm to ambient temperature and stir for 16 hours. Concentrate in vacuo to obtain a residue. Dilute the residue with ethyl acetate and extract with water. Separate the layers, dry the organic layer over $MgSO_4$, filter, and evaporate in vacuo to give the title compound: TLC $R_f$=0.32 (silica gel, 30% ethyl acetate/hexane).

PREPARATION 4

Synthesis of N-t-Butoxycarbonyl-N-(2-oxo-ethyl)-2,2-bis-phenyl-ethylamine

N-t-Butoxycarbonyl-2,2-bis-phenyl-ethylamine

Scheme B, step a

Combine 2,2-bis-phenyl-ethylamine (20.0 g, 100.0 mmol) and dichloromethane (200 mL) and cool in an ice-bath to 0° C. Add dimethylaminopyridine (1.0 g, 8.2 mmol) and di-t-butyl dicarbonate (22.0 g, 100.0 mmol). After the addition is complete warm to ambient temperature for 5 hours. Evaporate in vacuo to give a residue. Dissolve the residue in ethyl acetate and extract with 0.1M hydrochloric acid solution, water and saturated sodium chloride solution. Separate the organic layer and dry over $MgSO_4$, filter and evaporate in vacuo to obtain a residue. Chromatograph the residue on silica gel eluting with 10% ethyl acetate/hexane to give the title compound.

N-t-Butoxycarbonyl-N-allyl-2,2-bis-phenyl-ethylamine

Scheme B, step c

Combine N-t-butoxycarbonyl-2,2-bis-phenyl-ethylamine (2.0 g, 7.73 mmol) and tetrahydrofuran (20 mL) and cool in a dry-ice/acetone bath to −78° C. Slowly, add n-butyllithium (4.4 mL, 1.6M in hexane, 7.04 mmol) and allow to stand for 30 minutes. Add allyl bromide (0.7 mL, 8.09 mmol) maintaining the temperature at −78° C. Warm to ambient temperature and allow to stand for 1.5 hour and then heat to reflux for 5 hours. Cool to ambient temperature and allow to stand for 18 hours. Extract the reaction mixture with a saturated ammonium chloride solution and separate the layers. Extract the aqueous layer with diethyl ether and combine the organic layers. Extract the combine organic layer with water and saturated sodium chloride solution. Separate the organic layer and dry over $MgSO_4$, filter and evaporate in vacuo to obtain a residue. Chromatograph the residue on silica gel eluting with 5% ethyl acetate/hexane to give the title compound.

N-t-Butoxycarbonyl-N-(2-oxo-ethyl)-2,2-bis-phenyl-ethylamine

Scheme B, step d

Combine N-t-butoxycarbonyl-N-allyl-2,2-bis-phenyl-ethylamine (0.23 g, 0.68 mmol) and dichloromethane (10 mL) and methanol (0.5 mL). Cool the −78° C. Pass ozonized oxygen through the solution until a persistent light blue color is obtained. Pass nitrogen through the solution until the blue color dissipates. Add dimethyl sulfide (2.0 mL). Allow the reaction mixture to warm to ambient temperature and stir for 5.5 hours. Concentrate in vacuo to obtain a residue. Dilute the residue with ethyl acetate and extract with water. Separate the layers, dry the organic layer over $MgSO_4$, filter, and evaporate in vacuo to give the title compound.

The tachykinins are a class of neuropeptides which share a common C-terminus sequence, Phe-Xaa-Gly-Leu-Met-$NH_2$. The tachykinins are widely distributed in the peripheral and central nervous systems where they bind to at least three receptors types. The $NK_1$, $NK_2$, and $NK_3$ receptors are defined by the preferred binding affinity of substance P, neurokinin A (NKA), and neurokinin B (NKB), respectively.

The use of tachykinin antagonists is indicated as therapy for a variety of tachykinin-mediated diseases and conditions including: cystitis; bronchodilation; hypersensitivity reactions; the treatment of pain; peripheral neuropathy; post-herpetic neuralgia; adverse immunological reactions; respiratory diseases, such as asthma, bronchitis, cough, rhinitis, and allergies and the like; opthalmic diseases, such as conjuctivitis and vernal conjuctivitis; cutaneous diseases, such as contact dermatitis, atopic dermatitis, and urticaria; inflammatory diseases, such as rheumatoid arthritis and osteoarthritis, and the like; gastrointestinal conditions, such as Crohn's disease, emesis, and ulcerative colitis; conditions due to vasodilation, such as angina and migraine; and central nervous system diseases and conditions, such as anxiety, depression, psychosis, schizophrenia, dementia.

It is understood that tachykinin-mediated diseases and conditions are those diseases and conditions in which the tachykinins are involved, either in whole or in part, in their clinical manifestation(s). Moreover, the tachykinins involvement is not necessarily causative of a particular tachykinin-mediated disease and condition. Tachykinin antagonists are useful in controlling or providing therapeutic relief of those tachykinin-mediated diseases and conditions.

The present invention provides new and useful tachykinin antagonists of formula (1) or stereoisomers or pharmaceutically acceptable salts thereof. Particularly, the present invention provides compounds of formula (1) which are $NK_2$ receptor antagonists.

In a further embodiment, the present invention provides a method of treating tachykinin-mediated diseases and conditions in a patient in need thereof comprising administering to said patient a therapeutically effective amount of a compound of formula (1). Various diseases and conditions described to be treated herein, are well known and appreciated by those skilled in the art. It is also recognized that one skilled in the art may affect the associated diseases and conditions by treating a patient presently afflicted with the diseases or conditions or by prophylactically treating a patient afflicted with the diseases or conditions with a therapeutically effective amount of the compounds of formula (1).

As used herein, the term "patient" refers to a warm blooded animal such as a mammal which is afflicted with a particular tachykinin-mediated disease or condition. It is understood that guinea pigs, dogs, cats, rats, mice, horses, cattle, sheep, and humans are examples of animals within the scope of the meaning of the term.

As used herein, the term "therapeutically effective amount" of a compound of formula (1) refers to an amount which is effective in controlling tachykinin-mediated diseases and conditions. The term "controlling" is intended to refer to all processes wherein there may be a slowing, interrupting, arresting, or stopping of the progression of the diseases and conditions described herein, but does not necessarily indicate a total elimination of all disease and condition symptoms, and is intended to include prophylactic treatment of the tachykinin-mediated diseases and conditions.

A therapeutically effective amount can be readily determined by the attending diagnostician, as one skilled in the art, by the use of conventional techniques and by observing results obtained under analogous circumstances. In determining the therapeutically effective amount, the dose, a number of factors are considered by the attending diagnostician, including, but not limited to: the species of mammal; its size, age, and general health; the specific disease involved; the degree of or involvement or the severity of the disease; the response of the individual patient; the particular compound administered; the mode of administration; the bioavailability characteristic of the preparation administered; the dose regimen selected; the use of concomitant medication; and other relevant circumstances.

A therapeutically effective amount of a compound of formula (1) is expected to vary from about 0.1 milligram per kilogram of body weight per day (mg/kg/day) to about 100 mg/kg/day. Preferred amounts are able to be determined by one skilled in the art.

In effecting treatment of a patient afflicted with tachykinin-mediated diseases and conditions described above, a compound of formula (1) can be administered in any form or mode which makes the compound bioavailable in an effective amount, including oral and parenteral routes. For example, compounds of formula (1) can be administered orally, by inhalation of an aerosol or dry powder, subcutaneously, intramuscularly, intravenously, transdermally, intranasally, rectally, topically, and the like. Oral or inhalation administration is generally preferred for treatment of respiratory diseases and conditions, e.g. asthma. One skilled in the art of preparing formulations can readily select the proper form and mode of administration depending upon the particular characteristics of the compound selected, the disease or condition to be treated, the stage of the disease or condition, and other relevant circumstances. (Remington's Pharmaceutical Sciences, 18th Edition, Mack Publishing Co. (1990)).

The compounds of the present invention can be administered alone or in the form of a pharmaceutical composition in combination with pharmaceutically acceptable carriers or excipients, the proportion and nature of which are determined by the solubility and chemical properties of the compound selected, the chosen route of administration, and standard pharmaceutical practice. The compounds of the present invention, while effective themselves, may be formulated and administered in the form of their pharmaceutically acceptable salts, such as acid addition salts or base addition salts, for purposes of stability, convenience of crystallization, increased solubility and the like.

In another embodiment, the present invention provides pharmaceutical compositions comprising a therapeutically effective amount of a compound of formula (1) in admixture or otherwise in association with one or more pharmaceutically acceptable carriers or excipients.

The pharmaceutical compositions are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral, inhalation, parenteral, or topical use and may be administered to the patient in the form of tablets, capsules, aerosols, inhalants, suppositories, solution, suspensions, or the like.

The compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound of the present invention, the active ingredient, but may be varied depending upon the particular form and may conveniently be between 4% to about 70% of the weight of the unit. The amount of the compound present in compositions is such that a suitable dosage will be obtained. Preferred compositions and preparations according to the present invention may be determined by someone skilled in the art.

The tablets, pills, capsules, troches and the like may also contain one or more of the following adjuvants: binders such as microcrystalline cellulose, gum tragacanth or gelatin; excipients such as starch or lactose, disintegrating agents such as alginic acid, Primogel, corn starch and the like; lubricants such as magnesium stearate or Sterotex; glidants such as colloidal silicon dioxide; and sweetening agents such as sucrose or saccharin may be added or a flavoring agent such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the compounds of the present invention may be incorporated into a solution or suspension. These preparations should contain at least 0.1% of a compound of the invention, but may be varied to be between 0.1 and about 50% of the weight thereof. The amount of the compound of formula (1) present in such compositions is such that a suitable dosage will be obtained. Preferred compositions and preparations are able to be determined by one skilled in the art.

The compounds of the present invention may also be administered by inhalation, such as by aerosol or dry powder. Delivery may be by a liquefied or compressed gas or by a suitable pump system which dispenses the the compounds of the present invention or a formulation thereof. Formulations for administration by inhalation of compounds of formula (1) may be delivered in single phase, bi-phasic, or tri-phasic systems. A variety of systems are available for the administration by aerosol of the compounds of formula (1). Dry powder formulations are prepared by either pelletizing or milling the compound of formula (1) to a suitable particle size or by admixing the pelletized or milled compound of formula (1) with a suitable carrier material, such as lactose and the like. Delivery by inhalation includes the necessary container, activators, valves, subcontainers, and the like. Preferred aerosol and dry powder formulations for administration by inhalation can be determined by one skilled in the art.

The compounds of the present invention may also be administered topically, and when done so the carrier may suitably comprise a solution, ointment or gel base. The base, for example, may comprise one or more of the following: petrolatum, lanolin, polyethylene glycols, bee wax, mineral oil, diluents such as water and alcohol, and emulsifiers and stabilizers. Topical formulations may contain a concentration of the formula (1) or its pharmaceutical salt from about 0.1 to about 10% w/v (weight per unit volume).

The solutions or suspensions may also include one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

One skilled in the art can determine the $NK_1$ receptor and $NK_2$ receptor affinity in vitro as follows. The $NK_1$ receptor affinity of tachykinin antagonists is evaluated in guinea pig lungs (Keystone Biologicals, Cleveland, Ohio) and affinity for the $NK_2$ receptor is evaluated in HSKR-1 cells (which are mouse 3T3 fibroblasts expressing the human jejunal $NK_2$ receptor). Tissues or cells are homogenized with a Polytron in 15 volumes of 50 mM Tris-HCl buffer (pH 7.4, 4° C.) and centrifuged. The pellet is resuspended in Tris-HCl buffer and is centrifuged; the pellet is washed twice by resuspension. The final pellet is resuspended at a concentration of 40 mg/ml for tissues and 20 mg/ml for cells in incubation buffer and remains at room temperature for at least 15 min prior to use. Receptor binding is initiated by addition of 250 ul membrane preparation in duplicate to 0.1 nM of the following radioligands; $^{125}$I-Bolton Hunter Lys-3 labeled substance P and $^{125}$iodohistidyl-1-neurokinin A; in a final volume of 500 ul of buffer containing 50 mM Tris-HCl (pH 7.4 at room temperature), 0.1% bovine serum albumin, 2 mM $MnCl_2$, 40 ug/ml bacitracin, 4 $\mu$g/ml leupeptin and chymostatin, 10 $\mu$M thiorphan and various doses of the putative tachykinin antagonists. Incubations are performed at room temperature for 90 min ($NK_1$ receptor assays) or 2 hr ($NK_2$ receptor assay); binding is terminated by addition of 50 mM Tris-HCl buffer (pH 7.4, 4° C.) and filtration under vacuum through GF/B filters presoaked with 0.1% polyethyleneimine ($NK_1$ receptor assays) or 0.5% bovine serum albumin ($NK_2$ receptor assay). Filter bound radioactivity is quantitated in a gamma counter. Nonspecific binding is defined as binding in the presence of 1 $\mu$M substance P or neurokinin A. Specific binding is calculated by subtracting nonspecific binding from total binding. Competition of iodinated SP or NKA binding by test compounds or standards is expressed as a percentage of this maximum binding. $IC_{50}$ values (concentration required to inhibit 50% of receptor binding) are generated for each of the test compounds by nonlinear regression using an iterative curve fitting program (GraphPAD Inplot, San Diego, Calif.).

One skilled in the art can also determine the $NK_1$ receptor and $NK_2$ receptor affinity in vitro as follows. Tachykinin-mediated phosphatidylinositol (PI, inositol phosphate) accumulation is measured in UC11 or SKLKB82#3 cells in the presence and absence of $NK_1$ or $NK_2$ receptor antagonists, respectively. Tissues are incubated in Krebs-Henseleit buffer at 37° C. with 95% $O_2$–5% $CO_2$ gassing. Tissues are then incubated with fresh buffer containing 100 µCi of myo-[2-$^3$H(N)]inositol at 37° C. for 60 min with gentle gassing. After washing twice in 5 ml room temperature buffer containing 10 mM LiCl, tissues are incubated for 30 min at room temperature with a buffer change at 15 min. Buffer is removed and Krebs-Henseleit buffer (containing 40 µg/ml bacitracin, 4 µg/ml each of leupeptin and chymostatin, 0.1% bovine serum albumin and 10 µM of thiorphan and 10 mM of LiCl) including the test compound is added. After 15 min, SP is added to UC11 cells or NKA to SKLKB82#3 cells at various concentrations to start the reaction. After incubation for 60 min at room temperature the reaction is terminated by addition of 930 µl chloroform: methanol (1:2 by volume) to each tube, followed by 310 µl chloroform and 310 µl doubly distilled water. Samples are vortexed, centrifuged, and 0.9 ml of the aqueous (top) phase removed and added to 2 ml doubly distilled $H_2O$. The mixture is vortexed and loaded onto a 50% Bio-Rad AG 1-X8 (formate form, 100–200 mesh) exchange column (Bio-Rad Laboratories, Hercules, Calif.). The columns are washed, in order, with: 1) 10 ml doubly distilled water, 2) 5 ml of 5 mM disodium tetraborate/60 mM sodium formate, and 3) 5 ml of 1M ammonium formate/0.1M formic acid. The third elution is collected and 1 ml counted in 7 ml scintillation fluid. A 50 µl aliquot of the organic (bottom) phase is removed, dried in a scintillation vial and counted in 7 ml scintillation fluid.

The ratio of DPM in the aqueous phase aliquot (total inositol phosphates) to the DPM in the 50 µl organic phase aliquot (total [$^3$H]inositol incorporated) is calculated for each sample. Data are expressed as a percent of agonist-induced accumulation of [$^3$H]-inositol phosphates over basal levels. The ratios in the presence of test compound and/or standards are compared to the ratios for control samples (i.e. no stimulating agonist). Dose-response graphs are constructed and the ability of the test compounds to inhibit tachykinin-induced phosphatidyinositol turnover determined with the aid of a computer program. Data is expressed as percent stimulation of total inositol phosphate accumulation over basal levels and normalized to the maximum response produced by SP. Schild analysis is performed using dose response curves to obtain a value indicative of the strength of a competitive antagonist and is expressed as the $pA_2$, which is the negative logarithm of the molar concentration of antagonist which reduces the effect of a dose of agonist to one-half of that expected at the dose of agonist.

One skilled in the art can determine that the compounds of the present intention are $NK_1$ receptor antagonists in vivo by evaluating the compounds ability to inhibit SP-induced plasma protein extravasation in guinea pig trachea. SP-induced protein leakage through postcapillary venules is assessed by measuring Evans Blue dye accumulation in guinea pig trachea. Animals are anesthetized with pentobarbital then injected with Evans Blue dye (20 mg/kg, i.v., prepared in 0.9% NaCl solution). One minute after dye administration, the antagonist is administered (i.v.) followed by SP (0.3 nmole/kg, i.v.) and, after 5 min, excess dye removed from the circulation by transcardiac perfusion with 50 ml 0.9% NaCl solution. The trachea and primary bronchi are removed, blotted dry and weighed. Dye quantitation is performed spectrophotometrically (620 nM) after extracting tissues in formamide for 24 hr at 50° C. Values are subtracted from background (dye only, no agonist). $ED_{50}$ (dose of compound which inhibits SP-induced plasma protein extravasation by 50%) is calculated from linear regression analysis.

One skilled in the art can determine that the compounds of the present intention are $NK_2$ receptor antagonists in vivo by evaluating the compounds ability to inhibit NKA-induced respiratory effects. In addition, both $NK_1$ and $NK_2$ antagonism can be evaluated after administration of capsaicin, which is known to release both SP and NKA from airway sensory nerves. Antagonism of NKA and capsaicin induced respiratory effects in conscious guinea pigs is carried out as follows. In vivo experiments are performed using male Duncan Hartley guinea pigs (250–350 g). Changes in conscious breathing patterns are monitored in four animals simultaneously using modified whole body plethysmography consisting of four small plexiglass boxes each connected to a reference box via Validyne DP 45-16 differential pressure transducers. The 4 boxes are equipped with an air supply line (also used for aerosol delivery) and an exhaust air line. Supply and exhaust lines are of the same length and narrow bore and arise from a common supply chamber and vented to a common exhaust chamber. This system is used to ensure that fluctuations in supply air and atmospheric pressure remain in phase and be eliminated from the net signal by the differential pressure transducers. The analog pressure signals are digitalized via a Data Translation DT2821 A to D board. Data are collected at a rate of 100 samples/second/animal. Each cycle of pressure change is analyzed using the following parameters: rising and falling slope determined between minimum and maximum pressures, the ratio of rising over falling slope, and the magnitude of the change between initial trough pressure and peak cycle pressure. Using these values (and observing the animals) the pressure cycles are characterized into normal breaths, forced exhalations (apparent by abdominal heaving), significant respiratory events (SREs; usually coughs, less often sneezes or gasps which are characterized by transient, extremely large pressure increases which are distinguishable from noise) and movement/noise with a PCAT 286 running a System V UNIX operating system. Dyspnea is defined as a significant, sustained increase in plethysmograph pressure which is associated with an observable shift to labored breathing in the animal.

During the course of a typical experiment in which airway responsiveness to various bronchoconstricting agents is examined, aerosols are delivered for 19 min (0.33 ml/min) using a DeVilbiss Ultraneb 99 ultrasonic nebulizer and animals monitored during this time. Prior to nebulization, 1 min of resting breathing is collected to establish a baseline pressure. In preliminary experiments, various concentrations of the bronchoconstrictive agents are evaluated and the concentration chosen which maximized the number of animals exhibiting dyspnea but minimized the severity of the response. Hence, neurokinin A is delivered at a final concentration of 0.05%, and capsaicin, 0.001%. The vehicle for nebulization of all bronchoconstrictive agents is phosphate buffered saline (pH 7.4) which elicited no respiratory effects itself. Putative tachykinin antagonists are administered (i.v.) 20 min prior to onset of aerosol exposure.

What is claimed is:
1. A compound of the formula

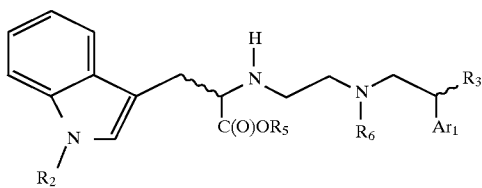

wherein
$Ar_1$ is a radical chosen from the group:

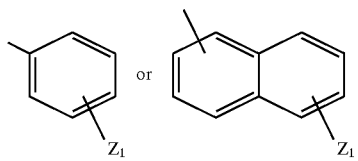

wherein
$Z_1$ is from 1 to 3 substituents each independently chosen from the group consisting of hydrogen, halogen, benzyloxy, hydroxy, $CF_3$, $C_1-C_4$ alkyl, and $C_1-C_4$ alkoxy;
$R_2$ is hydrogen, $C_1-C_4$ alkyl, or —CHO;
$R_3$ is hydrogen or a radical chosen from the group

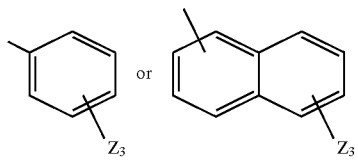

wherein
$Z_3$ is from 1 to 3 substituents each independently chosen from the group consisting of hydrogen, halogen, benzyloxy, hydroxy, $CF_3$, $C_1-C_4$ alkyl, and $C_1-C_4$ alkoxy;

$R_5$ is hydrogen, benzyl, or $C_1-C_4$ alkyl;
$R_6$ is hydrogen or —C(O)OR$_7$ wherein $R_7$ is benzyl or $C_1-C_4$ alkyl;
or stereoisomers, or pharmaceutically acceptable salt thereof.

2. A compound of claim 1 wherein $R_6$ is —C(O)OR$_7$.
3. A compound of claim 1 wherein $R_6$ is hydrogen.
4. A compound of claim 1 wherein $R_5$ is methyl.
5. A compound of claim 1 wherein the compound is 2-[(R)-2-(1H-Indol-3-yl)-1-carboxymethyl-ethylamino]-N-(t-butoxycarbonyl)-N-(2-phenyl-ethyl)-ethylamine.
6. A compound of claim 1 wherein the compound is 2-[(R)-2-(1H-Indol-3-yl)-1-carboxymethyl-ethylamino]-N-(2-phenyl-ethyl)-ethylamine.
7. A compound of claim 1 wherein the compound is 2-[(S)-2-(1H-Indol-3-yl)-1-carboxymethyl-ethylamino]-N-(t-butoxycarbonyl)-N-(2-phenyl-ethyl)-ethylamine.
8. A compound of claim 1 wherein the compound is 2-[(S)-2-(1H-Indol-3-yl)-1-carboxymethyl-ethylamino]-N-(2-phenyl-ethyl)-ethylamine.
9. A compound of claim 1 wherein the compound is 2-[(R)-2-(1H-Indol-3-yl)-1-carboxymethyl-ethylamino]-N-(t-butoxycarbonyl)-N-[2-[(4-benzyloxy)phenyl-ethyl]]-ethylamine.
10. A compound of claim 1 wherein the compound is 2-[(R)-2-(1H-Indol-3-yl)-1-carboxymethyl-ethylamino]-N-[2-[(4-benzyloxy)phenyl-ethyl]]-ethylamine.
11. A compound of claim 1 wherein the compound is 2-[(S)-2-(1H-Indol-3-yl)-1-carboxymethyl-ethylamino]-N-(t-butoxycarbonyl)-N-[2-[(4-benzyloxy)phenyl-ethyl]]-ethylamine.
12. A compound of claim 1 wherein the compound is 2-[(S)-2-(1H-Indol-3-yl)-1-carboxymethyl-ethylamino]-N-[2-[(4-benzyloxy)phenyl-ethyl]]-ethylamine.
13. A compound of claim 1 wherein the compound is 2-[(R)-2-(1H-Indol-3-yl)-1-carboxymethyl-ethylamino]-N-(t-butoxycarbonyl)-N-(2,2-bis-phenyl-ethyl)]-ethylamine.
14. A compound of claim 2 wherein the compound is 2-[(R)-2-(1H-Indol-3-yl)-1-carboxymethyl-ethylamino]-N-(2,2-bis-phenyl-ethyl)]-ethylamine.

* * * * *

UNITED STATES PATENT AND TRADEMARK OFFICE
CERTIFICATE OF CORRECTION

PATENT NO. : 5,864,045

DATED : January 26, 1999

INVENTOR(s) : Timothy P. Burkholder, Elizabeth M. Kudlacz, Tieu-Binh Le

It is certified that error appears in the above-identified patent and that said Letters Patent is hereby corrected as shown below:

Column 2, line 29, change "chose n" to -- chosen --.

Column 4, line 28, change "at the either" to -- at either --.

Column 6, line 59, start a new paragraph with "(S)-3-...".

Column 7, line 51, delete "p0".

Column 11, line 43, change "with in" to -- within --.

Column 12, line 25, change "diisopropylethylyamine" to -- diisopropylethylamine --.

Column 12, line 31, change "form" to -- from --.

Column 13, line 45, change "require" to -- requires --.

Column 13, line 50, change "is", first occurrence, to -- , in --.

Column 13, line 50, after "hydrogen" insert -- , --.

Column 14, line 11, change "litium" to -- lithium --.

Column 19, change the structure of Example 7:

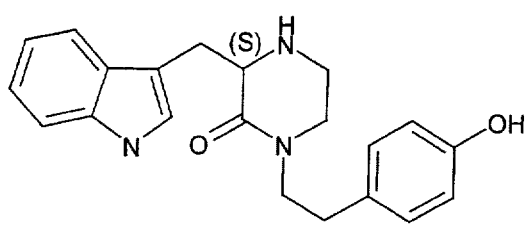

to

UNITED STATES PATENT AND TRADEMARK OFFICE
CERTIFICATE OF CORRECTION

PATENT NO. : 5,864,045

DATED : January 26, 1999

INVENTOR(s) : Timothy P. Burkholder, Elizabeth M. Kudlacz, Tieu-Binh Le

It is certified that error appears in the above-identified patent and that said Letters Patent is hereby corrected as shown below:

--

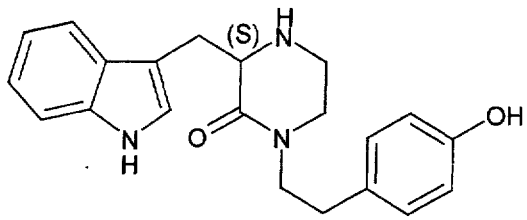

--.

Column 20, change the structure of Example 8:

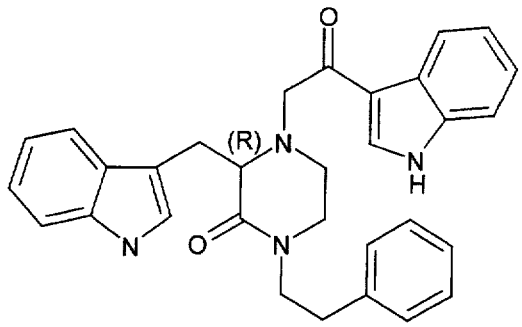

UNITED STATES PATENT AND TRADEMARK OFFICE
CERTIFICATE OF CORRECTION

PATENT NO. : 5,864,045
DATED : January 26, 1999
INVENTOR(S) : Timothy P. Burkholder, Elizabeth M. Kudlacz, Tieu-Binh Le It is certified that error appears in the above-identified patent and that said Letters Patent is hereby corrected as shown below:

to --

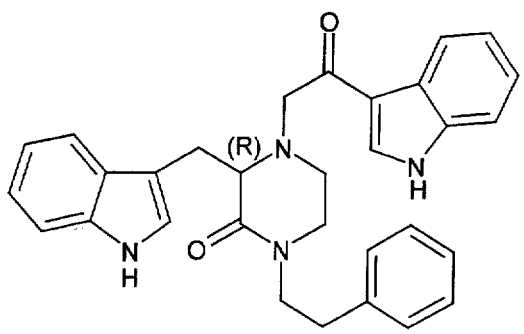

Column 25, line 29, change "form" to -- from --.
Column 25, line 43, change "form" to -- from --.
Column 26, line 9, change "a at" to -- at a --.
Column 31, line 58, change "the the" to -- the --.

Signed and Sealed this

Twenty-sixth Day of September, 2000

Attest:

Q. TODD DICKINSON

*Attesting Officer*  *Director of Patents and Trademarks*